(12) United States Patent
Depinho et al.

(10) Patent No.: US 7,371,515 B2
(45) Date of Patent: May 13, 2008

(54) IDENTIFYING AND CHARACTERIZING GENES

(75) Inventors: Ronald A. Depinho, Brookline, MA (US); Lynda Chin, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 297 days.

(21) Appl. No.: 10/112,503

(22) Filed: Mar. 28, 2002

(65) Prior Publication Data

US 2003/0003478 A1 Jan. 2, 2003

Related U.S. Application Data

(60) Provisional application No. 60/279,506, filed on Mar. 28, 2001.

(51) Int. Cl.
*C12Q 1/70* (2006.01)
*C12N 15/00* (2006.01)
*C12N 15/63* (2006.01)
*A01N 63/00* (2006.01)

(52) U.S. Cl. .................. 435/5; 435/320.1; 435/455; 424/93.21

(58) Field of Classification Search .............. 435/5, 435/320.1, 325, 455; 424/93.21
See application file for complete search history.

(56) References Cited

U.S. PATENT DOCUMENTS

| 5,919,997 | A | 7/1999 | Beach et al. ............... 800/18 |
| 6,639,121 | B1 | 10/2003 | DePinho et al. ........... 800/10 |

FOREIGN PATENT DOCUMENTS

WO    WO 97/20463    * 6/1997

OTHER PUBLICATIONS

Oberg et al (2004) Loss of mismatch of MHC Class I is sufficient to trigger NK cell-mediated rejection of resting lymphocytes in vivo-role of KARAP/DAP12-dependent and independent pathways. Eur. J. Immunol. 34:1646-1653.*
Walther et al. (1996) Cell Type specific and inducible promoters for vectors in gene therapy as an approach for cell targeting. J. Mol Med. 74:379-392.*
Kolb et al. (1999) Insertion of a foriegn gene into the beta-casein locus by Cre-mediated site-specific recombination. Gene 227:21-31.*
Houdebine. (2000) Transgenic animal bioreactors. Transgenic Research. 9:305-320.*
Houdebine, L-M., 2002 (Journal of Biotechnology, vol. 98, p. 145-160).*
Leiter et al. (2002) Diabetologia 45:296-308.*
Efrat et al., 1995, PNAS, vol. 92, pp. 3576-3580.*
Allen, et al., "Complementation tagging of cooperating oncogenes in knockout mice", Cancer Bio., 7:299-306 (1996).
Berns, et al., "Identification and Characterization of Collaborating Oncogenes in Compound Mutant Mice", Cancer Res., 59:1773s-1777s (1999).
Bedigan et al., "Spontaneous and Induced Leukemias of Myeloid Origin in Recombinant Inbred BXH Mice," *J. Virol.*, 1984, 51(3):586-594.
Chin et al., "Cooperative effects of *INK4a* and *ras* in melanoma susceptibility in vivo," *Genes Dev.*, 1997, 11:2822-2834.
Chin et al., "Essential role for oncogenic Ras in tumour maintenance," *Nature*, 1999, 400:462-472.
Clark et al., "Genomic analylsis of metastasis reveals an essential role for RhoC," *Nature*, 2000, 406:532-535.
Duggan et al., "Expression profiling using cDNA microarrays," *Nature Genetics Suppl.*, 1999, 21:10-14.
Fisher et al., "Development of a flexible and specific gene delivery system for production of murine tumor models," *Oncogene*, 1999, 18(38):5253-5260.
Ganss et al., "A cell-specific enhancer far upstream of the mouse tyrosinase gene confers high level and copy number-related expression in transgenic mice," *EMBO J.*, 1994, 13(13):3083-3093.
Gilbert et al., "Susceptibility of AKXD Recombinant Inbred Mouse Strains to Lymphomas," *J. Virol.*, 1993, 67(4):2082-2090.
Hahn et al., "Creation of human tumour cells with defined genetic elements," *Nature*, 1999, 400:464-468.
Haupt et al., "Novel Zinc Finger Gene Inplicated as *myc* Collaborator by Retrovirally Accelerated Lymphomagenesis in Eμ-*myc* Transgenic Mice," *Cell*, 1991, 65:753-763.
Herlyn, *Molecular and Cellular Biology of Melanoma*, 1993, R. G. Landes Company, Austin (Table of Contents only).
Kistner et al., "Doxycycline-mediated quantitative and tissue-specific control of gene expression in transgenic mice," *Proc. Natl. Acad. Sci. USA*, 1996, 93:10933-10938.
Malumbres and Pellicer, "Ras Pathways to Cell Cycle Control and Cell Transformation," *Frontiers in Bioscience*, 1998, vol. 3, 49 pgs.

(Continued)

Primary Examiner—Shin-Lin Chen
(74) Attorney, Agent, or Firm—Ropes & Gray LLP; Jane T. Gunnison

(57) ABSTRACT

The invention provides methods and materials for identifying and characterizing genes related to phenotypes such as cancer and cell survivability. Also provided in the invention are cells and transgenic, non-human mammals that can be used in these methods.

7 Claims, 11 Drawing Sheets

OTHER PUBLICATIONS

Nesbit et al., "Basic fribroblast growth factor induces a transformed phenotype in normal human melnocytes," *Oncogene*, 1999, 18(47):6469-6476.

Paddison et al., "Stable suppression of gene expression by RNAi in mammalian cells," *Proc. Natl. Acad. Sci. USA*, 2002, 99(3):1443-1448.

Pierucci et al., "NGF-withdrawal induces apoptosis in pancreatic beta cells in vito," *Diabetologia*, 2001, 44:1281-1295.

Rigel et al., "Lifetime risk for development of skin cancer in the U.S. population: Current estimate is now 1 in 5," *J. Am. Acad. Dermatol.*, 1996, 35(6):1012-1013.

Shimizu et al., "High Expression of Macrophage Migration Inhibitory Factor in Human Melanoma Cells and Its Role in Tumor Cell Growth and Angiogenesis," *Biochem. Biphys. Res. Comm.*, 1999, 264:751-758.

Shirasawa et al., "Altered Growth of Human Colon Cancer Cell Lines Disrupted at Activate Ki-*ras*," *Science*, 260:85-88.

Skobe et al., "Induction of tumor lymphangiogenesis by VEGF-C promotes breast cancer metastasis," *Nature Medicine*, 2001, 7(2):192-198.

Thomson et al., "Differentiation Antigens of Melanocytes and Melanoma: Analysis of Melanosome and Cell Surface Markers of Human Pigmented Cells With Monoclonal Antibodies," *J. Invest. Dermatol.*, 1988, 90:459-466.

Tobin et al., "Consequences of altered TGF-β expression and responsiveness in breast cancer: evidence for autocrine and paracrine effects," *Oncogene*, 2002, 21:108-118.

Tokunaga et al., "Ribozyme-mediated inactivation of mutant K-ras oncogene in a colon cancer cell line," *Br. J. Cancer*, 2000, 83(6):833-839.

van Lohuizen et al., "Identification of Cooperating Oncogenes in Eµ-*myc* Transgenic Mice by Provirus Tagging," *Cell*, 1991, 65:737-752.

Velculescu, "Tantalizing Transcriptions—SAGE and Its Use in Global Gene Expression Analysis," *Science*, 1999, 286:1491-1492.

ClonTech Laboratories Inc., "Tet-Inducible Retroviral cDNA Library User Manual," PT3352-1 (PR13438), Catalog # HL8500BC, published Mar. 16, 2001, pp. 1-23.

Lewandoski, M., "Conditional Control of Gene Expression in the Mouse," Nature Reviews, 2:743-755 (2001).

Valentis Home page, Geneswitch Systems Press Releases. Apr. 12, 2005. <http://www.geneswitch.com/press/index.html>.

Indra et al., "Temporally-controlled site-specific mutagenesis in the basal layer of the epidermis: comparison of the recombinase activity of the tamoxifen-inducible Cre-ER(T) and Cre-ER(T2) recombinases," Nucleic Acids Research, 27:4324-4327 (1999).

"Mouse genetics and transgenics," A Practical Approach Series Book, Jackson & Abbott (edtrs); Oxford university Press (2000), p. 218 (9.1.2) and 220 (9.1.4).

"Manipulating the Mouse Embryo", Hogan, Beddington, Costantini & Lacy (2nd Ed.); CSHL Press (1994), p. 293 paragraphs 1 & 2.

"Manipulating the Mouse embryo", Nagy, Gertsenstein, Vintersten and Behringer (3rd Ed.); CSHL Press (2003), p. 511 and 515.

Moody et al., "Conditional activation of Neu in the mammary epithelium of transgenic mice results in reversible pulmonary metastasis," Cancer Cell, 2:451-461 (2002).

Huettner et al., "Reversibility of acute B-cell leukaemia induced by BCR-ABL1," Nature Genetics, 24:57-60 (2000).

Fisher et al., "Induction and apoptosis regression of lung adenocarcinomas by regulation of a K-Ras transgene in the presence and absence of tumor suppressor genes," Genes & Development, 15:3249-3262 (2001).

Ji et al., "The impact of human EGFR kinase domain mutations on lung tumorigenesis and in vivo sensitivity to EGFR-targeted therapies," Cancer Cell, 9:485-495 (2006).

Chin et al., "Essential role for oncogenic Ras in tumor maintenance," Nature, 400: 468-472 (1999).

\* cited by examiner

Figure 7

Figure 9

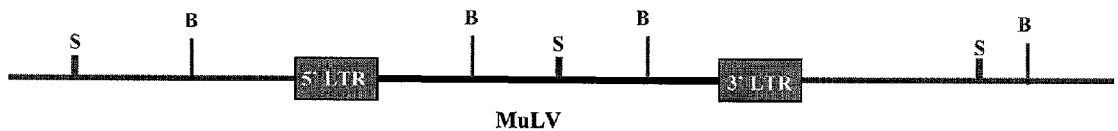

MuLV

Each integration event generates two flanking Proviral-Tagged Sequences (PTS).

Genomic DNA digested with SacII or Bam HI produces linear fragments containing PTS which can be re-circularized by T4 DNA Ligase.

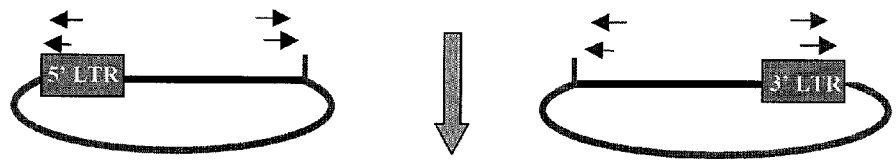

Each circularized PTS is amplified using nested MuLV-specific primers as indicated.

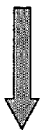

Resultant amplicons (PTS) are subcloned into T/A vector and sequenced bi-directionally using standard primers.

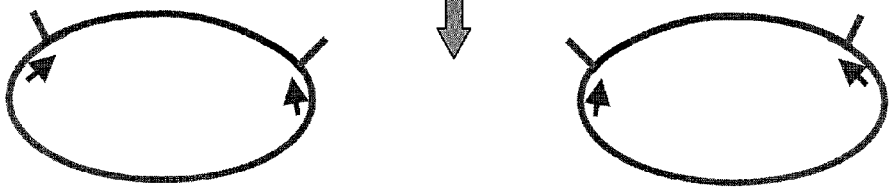

IDENTIFYING AND CHARACTERIZING GENES

RELATED APPLICATIONS

This application claims priority to U.S. Provisional Application Ser. No. 60/279,506, filed Mar. 28, 2001.

TECHNICAL FIELD

This invention relates to methods and materials for identifying genes involved in phenotypes such as cancer genesis, cancer progression, cancer maintenance, metastasis, and cell survival.

BACKGROUND

The impact of cancer on our society cannot be understated. In addition, to compound matters, the incidence of some cancers is increasing. For example, the incidence of melanoma as a cancer type is rising at a rate second only to lung cancer in women (see Rigel et al., *J. Am. Acad. Derm.* 35:1012, 1996). This crisis is compounded by the facts that, in contrast to most solid tumor types, melanoma affects a much younger population, metastasizes early in the course of disease, and fails to respond to current therapeutic regimens (see Herlyn, *Molecular and Cellular Biology for Melanoma*, Austin, R. G. Landes, 1993).

Despite the long history of clinical and research efforts directed towards understanding cancer, surprisingly little is known about the genetic lesions responsible for its genesis, progression, and clinical behavior. For example, in the case of melanoma, although many genes have been implicated in the genesis of this disease, only the INK4a and RAS genes have been shown to be true etiologic lesions in a formal genetic sense (Chin et al., *Genes Devel.* 11:2822, 1997). Moreover, advanced malignancy, which is among the most daunting conditions a clinician can face, represents the phenotypic endpoint of many successive genetic lesions that affect many oncogene and tumor suppressor gene pathways. Lesions that lead to such a condition, therefore, may differ from those required to maintain it. These mutations will represent rational therapeutic targets in the treatment of cancer.

SUMMARY

In a first aspect, the invention provides methods of identifying cancer (for example, skin (e.g., melanoma), lung, prostate, breast, colorectal, liver, pancreatic, brain, testicular, ovarian, uterine, cervical, kidney, thyroid, bladder, esophageal, hematological (e.g., leukemia), or lymphatic cancer)-related genes. These methods involve (a) maintaining cells in which tumorigenicity is dependent upon the expression of an inducible oncogene under conditions in which expression of the oncogene is not induced; (b) introducing into the cells a nucleic acid molecule that integrates into the genomes of the cells, and thereby tags the loci at which it integrates; (c) identifying cells in which tumorigenicity has been induced by integration of the nucleic acid molecule; and (d) identifying genes that have been tagged by the integrated nucleic acid molecule as cancer-related genes.

The cells used in these methods (e.g., epithelial cells, endothelial cells, or skin cells such as melanocytes) can include a mutation that renders them susceptible to tumorigenicity. For example, in the case of melanocytes, the cells can include a mutation in the INK4a/ARF gene (e.g., the cells can be heterozygous or homozygous for a INK4a/ARF gene mutation). The INK4a/ARF gene encodes two polypeptides, $p16^{INK4a}$ and $p19^{ARF}$. A mutation in the INK4a/ARF gene can disrupt expression of $p16^{INK4a}$, $p19^{ARF}$, or both $p16^{INK4a}$ and $p19^{ARF}$. In addition, the cells can contain other mutations such as mutations in the PTEN gene (e.g., the cells can be $PTEN^{+/-}$ or $PTEN^{-/-}$) or mutations in the Rb gene (e.g., the cells can be $Rb^{+/-}$ or $Rb^{-/-}$). Further, the cells can contain any combination of mutations (e.g., the cells can be null for $p16^{INK4a}$, $p19^{ARF}$, and Rb). The oncogene in these methods can be any dominant oncogene, for example, activated ras. Alternatively, a tumor suppressor gene can be used. The integrated nucleic acid molecule can include a retroviral vector, for example, the Moloney retrovirus (MuLV).

Induction of tumorigenicity by integration of the nucleic acid molecule in these methods can be determined, for example, by injecting a cell containing an integrated nucleic acid molecule into a non-human mammal (e.g., a mouse) and monitoring the mammal for development of a tumor. Alternatively, a soft agar assay or any of the other assays described herein can be employed.

The cells used in the methods of the invention can contain any inducible gene system. For example, they can include (a) a first expression construct including a gene encoding a tetracycline transactivator (henceforth denoting both standard tetracycline-OFF and reverse tetracycline-ON versions) operably linked to a tissue-specific promoter (e.g., in the case of melanoma, a tyrosinase promoter), and (b) a second expression construct including an oncogene operably linked to a promoter that is regulated by the tetracycline transactivator and tetracycline (or a tetracycline analogue such as doxycycline). Tetracycline analogues are compounds that function in a manner similar to tetracycline when used in a tetracycline regulatory system described herein. The first and second expression constructs can be stably integrated into the genomes of the cells. Alternatively, the first and second expression constructs can be contained within a single expression construct that is stably integrated into the genomes.

In another aspect, the invention provides a method for testing the effect of a candidate cancer-related gene on tumorigenicity. This method employs an inducible expression system that can be, for example, the tetracycline-based system described herein. The method involves (a) producing a transgenic non-human mammal (e.g., a mouse) containing cells in which (i) a first expression construct containing a gene encoding a reverse tetracycline transactivator operably linked to a promoter, such as any tissue or cell type-specific promoter (e.g., a tyrosinase promoter in the case of melanoma; a TRP2 promoter in the case of melanocytes; an MMTV or WAP promoter in the case of breast cells and/or cancers; a Villin or FABP promoter in the case of intestinal cells and/or cancers; a RIP promoter in the case of pancreatic beta cells; a Keratin promoter in the case of keratinocytes; a Probasin promoter in the case of prostatic epithelium; a Nestin or GFAP promoter in the case of CNS cells and/or cancers; a Tyrosine Hydroxylase or S100 promoter in the case of neurons; and an Alpha myosin promoter in the case of cardiac cells) or any general promoter (e.g., the cytomegalovirus (CMV) promoter), and (ii) a second expression construct containing the candidate cancer-related gene operably linked to a promoter that is regulated by the reverse tetracycline transactivator and tetracycline (or a tetracycline analogue, for example, doxycycline), are stably integrated into the genome, and (b) observing the mammal in the presence and absence of the tetracycline (or analogue thereof) for the development, maintenance, or progression of a tumor that is affected by the presence or absence of the tetracycline (or analogue thereof).

Such testing also can be carried out in cells (e.g., human cells) that are engineered to contain an inducible oncogene and endowed with tumorigenic capacity by the presence of an appropriate combination of oncogenes, tumor suppressor genes, and/or telomerase. The candidate cancer-related gene used in these methods can be one that is identified using the methods described herein. Also, this and other methods of the invention can employ any inducible oncogene system (e.g., one based on the metallothionien promoter or an estrogen receptor fusion) in place of that described above.

In a further aspect, the invention provides a cell containing (a) a first expression construct containing a gene encoding a reverse tetracycline transactivator operably linked to a tissue or cell type-specific promoter, (b) a second expression construct including an oncogene operably linked to a promoter that is regulated by the reverse tetracycline transactivator and tetracycline (or a tetracycline analogue such as doxycycline), and (c) a retroviral vector. The first and second expression constructs and the retroviral vector are stably integrated into the genome the cell.

In another aspect, the invention provides a transgenic, non-human mammal (e.g., a mouse, rat, or rabbit) having stably integrated into the genome of its cells (a) a first expression construct including a gene encoding a reverse tetracycline transactivator operably linked to a tissue-specific, cell type-specific, or general promoter, (b) a second expression construct including a candidate cancer-related gene operably linked to a promoter that is regulated by the reverse tetracycline transactivator and tetracycline (or a tetracycline analogue such as doxycycline). The candidate cancer-related gene used in this method can be one that is identified using the methods described herein.

In yet a further aspect, the invention provides a method of determining the efficacy of a candidate compound in preventing or treating cancer (e.g., skin (e.g., melanoma), lung, prostate, breast, colorectal, liver, pancreatic, brain, testicular, ovarian, uterine, cervical, kidney, thyroid, bladder, esophageal, hematological (e.g., leukemia), or lymphatic cancer). This method involves administering to the transgenic non-human mammal described herein a candidate compound and observing the effect of the compound on tumor development, maintenance, or progression in the mammal.

The invention provides several advantages. For example, the cancer models and methods of gene pathway dissection of the invention enable the identification and validation of tumor genes that function in particular stages of disease, in specific pathways, for example, genes required for tumor development, maintenance, progression, and/or metastasis in vivo. This is very important, because advanced malignancy represents the phenotypic endpoint of many successive genetic lesions that affect many oncogene and tumor suppressor gene pathways, and lesions that lead to such a condition may differ from those required to maintain it. Thus, for example, approaches that focus on genes and pathways involved in tumor maintenance, rather than initial tumor development, may lead to the development of better anti-cancer therapies and diagnostics for advanced disease. Alternatively, genes that are identified as being involved in initiation of cancer can be used in the discovery of therapies and diagnostics relating to prevention or early control of disease.

In another aspect, the invention features a method of identifying a cancer-related gene. The method includes (a) providing cells in which tumorigenicity is dependent upon expression of an oncogene; (b) maintaining the cells under conditions wherein the cells do not express the oncogene, the cells being tumorigenic when the oncogene is expressed; (c) introducing into the cells a nucleic acid molecule that integrates into the genomes of the cells, thereby tagging the loci at which the nucleic acid molecule integrates; (d) identifying a cell in which tumorigenicity has been induced by integration of the nucleic acid molecule; and (e) identifying, as the cancer-related gene, a gene that has been tagged in the cell of (d) by the integrated nucleic acid molecule. The cells of (a) can contain a mutation in the INK4a/Arf gene. The oncogene can be ras. The integrated nucleic acid molecule can contain a retroviral vector sequence. The cells can be melanocytes. Step (d) can include introducing a cell produced in step (c) into a non-human mammal and monitoring the mammal for development of a tumor. Step (d) can include a soft agar assay of tumorigenicity. The cells of (a) can contain: (a) a first expression construct comprising a gene encoding a reverse tetracycline transactivator operably linked to a tissue- or cell type-specific promoter or a general promoter; and (b) a second expression construct comprising the oncogene operably linked to a promoter that is regulated by the reverse tetracycline transactivator and tetracycline or a tetracycline analogue; wherein the first and second expression constructs are stably integrated into the genome of the cells.

In another aspect, the invention features a method of identifying a cancer-related gene. The method includes (a) providing cells, wherein the cells were obtained by: (i) altering the genome of a tumor cell such that at least one oncogene required for the tumorigenicity of the tumor cell is not expressed or (ii) altering the genome of a tumor cell such that at least one tumor suppressor gene that prevents the tumorigenicity of the tumor cell is expressed; (b) introducing into the cells a nucleic acid molecule that integrates into the genomes of the cells, thereby tagging the loci at which the nucleic acid molecule integrates; (c) identifying a cell in which tumorigenicity has been induced by integration of the nucleic acid molecule; and (d) identifying, as the cancer-related gene, a gene that has been tagged in the cell of (c) by the integrated nucleic acid molecule. The tumor cell can be a human tumor cell. The at least one oncogene can be ras. The at least one tumor suppressor gene can be an INK4a/Arf gene. The nucleic acid molecule can be a retroviral vector sequence. Step (c) can include introducing a cell produced in step (b) into a non-human mammal and monitoring the mammal for development of a tumor. Step (c) can include a soft agar assay of tumorigenicity.

Another aspect of the invention features a method of identifying a gene related to a given phenotype. The method includes (a) providing cells in which a given phenotype is dependent upon expression of a gene, (b) maintaining the cells under conditions wherein the cells do not express the gene, the cells exhibiting the given phenotype when the gene is expressed; (c) introducing into the cells of (b) a nucleic acid molecule that integrates into the genomes of the cells, thereby tagging the loci at which the nucleic acid molecule integrates; (d) identifying a cell in which the given phenotype has been induced by integration of the nucleic acid molecule; and (d) identifying, as the gene related to the given phenotype, a gene that has been tagged in the cell of (d) by the integrated nucleic acid molecule. The given phenotype can be tumorigenicity, the ability to metastasize, or cell survivability. The nucleic acid molecule can contain a retroviral vector sequence.

Another aspect of the invention features a method of identifying a gene related to a given phenotype. The method includes (a) providing cells, wherein the cells were obtained by: (i) altering the genome of a cell exhibiting the given phenotype such that at least one gene required for the given phenotype is not expressed in the cell, or (ii) altering the genome of a cell exhibiting the given phenotype such that at least one suppressor gene that prevents the phenotype is expressed in the cell; (b) introducing into the cells a nucleic acid molecule that integrates into the genomes of the cells thereby tagging the loci at which the nucleic acid molecule integrates; (c) identifying a cell in which the phenotype has been induced by integration of the nucleic acid molecule; and (d) identifying, as the gene related to the given phenotype, a gene that has been tagged in the cell of (c) by the integrated nucleic acid molecule. The given phenotype can be tumorigenicity, the ability to metastasize, or cell survivability. The nucleic acid molecule can contain a retroviral vector sequence.

Another aspect of the invention features a method of identifying a cancer-related gene. The method includes (a) providing cells in which metastasis of the cells is dependent upon expression of a gene, (b) maintaining the cells under conditions wherein the cells do not express the gene, wherein the cells metastasize within a mammal when the gene is expressed; (c) introducing into the cells a nucleic acid molecule that integrates into the genomes of the cells, thereby tagging the loci at which the nucleic acid molecule integrates; (d) identifying a cell in which the ability to metastasize has been induced by integration of the nucleic acid molecule; and (e) identifying, as a cancer-related gene, a gene that has been tagged in the cell of (d) by the integrated nucleic acid molecule.

Another aspect of the invention features a method of identifying a cancer-related gene. The method includes (a) providing cells, wherein the cells were obtained by: (i) altering the genome of a cell exhibiting the ability to metastasize such that at least one gene required for the ability to metastasize is not expressed, or (ii) altering the genome of a cell exhibiting the ability to metastasize such that at least one suppressor gene that prevents the ability to metastasize is expressed in the cell; (b) introducing into the cells a nucleic acid molecule that integrates into the genomes of the cells, thereby tagging the loci at which the nucleic acid molecule integrates; (c) identifying a cell in which the ability to metastasize has been induced by integration of the nucleic acid molecule; and (d) identifying, as the cancer-related gene, a gene that has been tagged in the cell of (c) by the integrated nucleic acid molecule.

Other features and advantages of the invention will be apparent from the following detailed description, the drawings, and the claims.

DESCRIPTION OF THE DRAWINGS

FIG. 7 is a photomicrograph showing that parental uninfected R545 cell lines will generate dermal tumors in SCID mice maintained on doxycycline. Top: Tumor #11 (see Table 1), measuring 0.4 cm×0.4 cm from MuLV infected cells, OFF doxycycline induction; Bottom: Tumor measuring 1.2 cm×1.3 cm from uninfected parental R545 cells on doxycycline.

FIG. 9 is a schematic representation of IPCR methodology for cloning of provirally-tagged sequences. B=BamHI; S=SacII.

DETAILED DESCRIPTION

Figure 1:
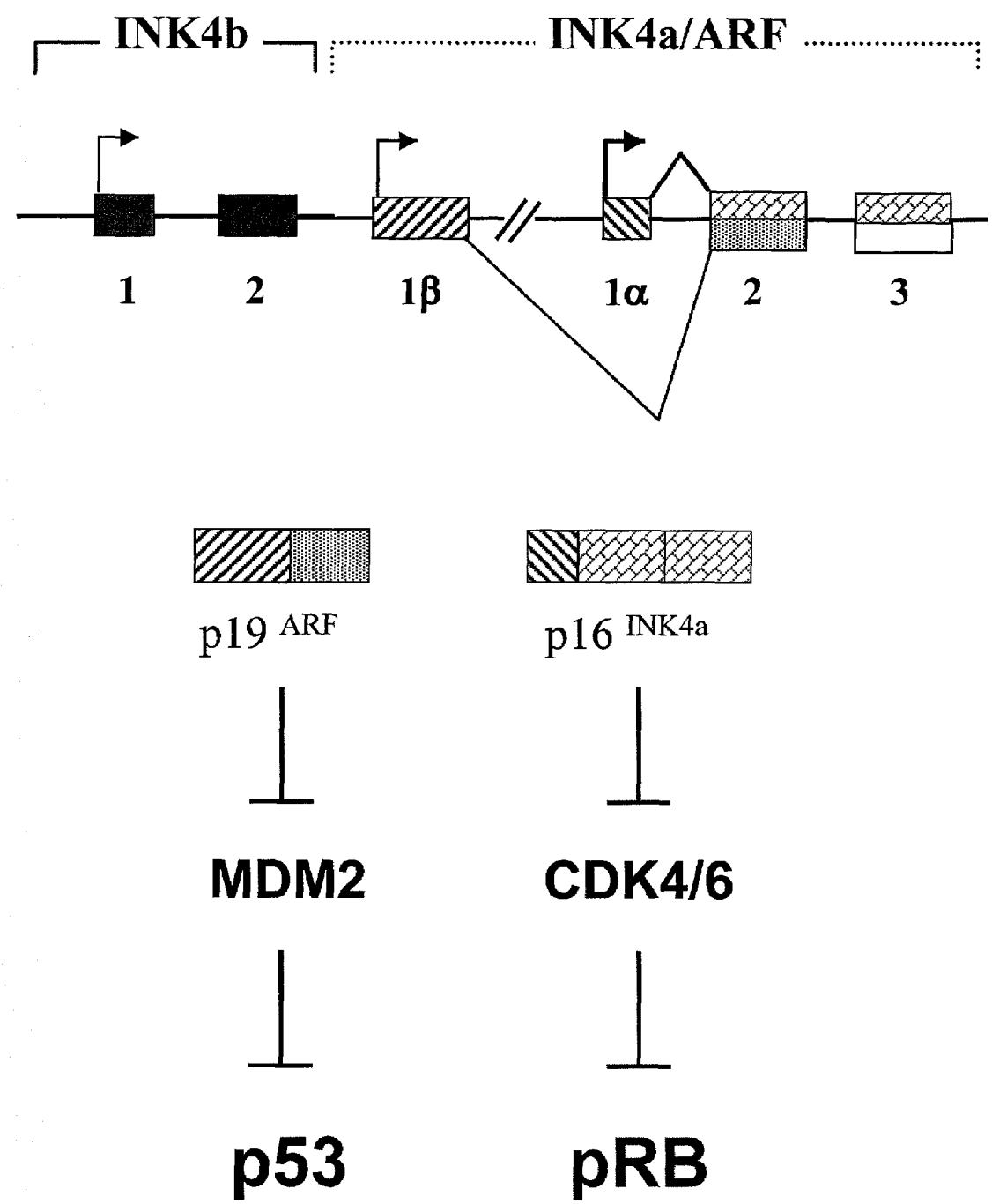
FIG. 1 is a schematic representation of the 9p21 locus in humans.

The invention provides methods of using in vivo and in vitro model systems to identify and characterize genes that are involved in tumor development, maintenance, progression, and/or metastasis. The methods of the invention are focused around the use of cells that require the activation (or inactivation) of a gene for the cells to become tumorigenic. As is discussed further herein, these cells can be engineered to be "one hit," i.e., one mutation, away from being tumorigenic. A nucleic acid molecule (e.g., a retroviral vector) is integrated into the genomes of these cells, and those cells that become tumorigenic because of the integration are evaluated further.

The cells can be analyzed for tumorigenicity by, for example, implantation into an animal (e.g., a nude mouse) and monitoring the animal for tumor formation. If an implanted cell gives rise to a tumor, the insertion site in the genome of the cell is characterized (e.g., by sequence analysis) to identify any gene or genes that have been activated (or inactivated) due to the insertion. Genes that are identified in this manner are candidates for involvement in tumor development, maintenance, progression, and/or metastasis, and can be further evaluated in animal model systems as is described herein.

The methods of the invention also employ inducible animal models of cancer as systems for cancer gene discovery. The construction of a cancer-prone animal harboring a regulatory switch controlling the expression of a dominant acting oncogene, for example, provides an in vivo model in which one can demonstrate that continued expression of the oncogene in fully formed tumors is required for maintaining tumorigenicity and tumor viability. In addition, such a model facilitates the establishment of in vitro cancer cell line model systems that similarly require expression of such oncogenes for tumorigenicity and tumor maintenance. Thus, when such an oncogene is not expressed (i.e., the regulatory switch is off), these cell lines represent clonal populations of cells having genomes that have sustained all the necessary alterations, except one, for a fully-transformed or malignant state. Taking advantage of these clonal populations, having genomes that are "one hit" away from being fully transformed (i.e., capable of tumorigenicity and maintenance in vivo), one can select for gain or loss of function mutations arising as consequences of insertions (e.g., proviral insertions) that can bypass dependency on the switchable oncogenic lesion. Genes that are activated or inactivated by such insertional mutagenesis can be identified by cloning and sequencing of insertion-tagged genomic sequences. With this "one-hit" Mammalian Second Site Suppressor (MaSS) screen, all candidate genes will likely be functioning either in the same pathway, downstream or upstream, of the switchable oncogene, or in a parallel pathway, with a similar function. Thus, the "one-hit"-MaSS screen of the invention not only allows rapid identification of genes that function in a specific pathway, but also predicts "escape" mechanisms via parallel pathways. Such "escape" pathways will likely represent resistance mechanisms to drug(s) that target the inducible oncogene.

Any dominant acting oncogene that plays a role in tumor development, maintenance, progression, and/or metastasis in vivo can be used in the invention. For example, oncogenes such as EGFR, BDNF, HER2/Neu, erb-B2, TGFβ, RhoC, VEGF-C, KRAS, HRAS and AKT, and their activated forms can be used. As a specific example, and as is described further herein, the RAS oncogene can be used in the methods of the invention. One can generate tumor cell lines derived from tumor-prone mutant mice having a regulated switch controlling expression of a dominant acting oncogene along known or novel pathways, select for gain or loss of function lesions that confer a desired phenotype either in vivo or in vitro (for example, enhanced tumorigenicity in an explant model, tumor maintenance in a host, motility/angiogenic potency in vitro, or tumor invasion or metastasis in vivo), and then identify specific candidates that function in these pathways by MaSS. These candidates can then be tested in vitro and validated in the same model in vivo as therapeutic targets.

The methods and materials provided herein can be used to identify cancer-related genes from human cells. For example, ectopic expression of the telomerase catalytic subunit (hTERT) in combination with two oncogenes (the simian virus 40 large and small T oncoprotein and an oncogenic allele of H-ras) can lead to direct tumorigenic conversion of normal human epithelial and fibroblast cells (Hahn et al. Nature, 400(6743):464-8, 1999). Thus, human tumor cells can be created by introducing this combination with the exception that H-RAS is expressed under an inducible vector (e.g., tet-regulated). Once tumorigenic conversion occurs, RAS expression can be switched off. Switching off RAS can render the human tumor cells non-tumorigenic, thus creating human cells that are "one-hit" away from being tumorigenic. With such cells, a MaSS screen can be performed to identify genes equivalent to RAS.

In addition, fully-established tumor cells (e.g., mouse or human tumor cells) can be somatically altered to inactivate a dominant acting oncogene (e.g., RAS) so that a cell that is "one-hit" away from tumorigenicity is created. For example, the activated Ki-ras genes in human colon carcinoma cell lines such as DLD-1 and HCT 116 can be disrupted by homologous recombination as described elsewhere (Shirasawa et al., Science, 260(5104):85-8, 1993). Somatic inactivation of gene expression can be accomplished using other standard methods such as ribozyme-mediated inactivation (see Tokunaga et al., Br. J. Cancer, 83(6):833-9, 2000) and RNAi (see Paddison et al., PNAS, 99(3): 1443-1448, 2002). Once the expression of an oncogene gene required for tumorigenicity has been reduced, the cells can be used in a MaSS Screen to identify cancer-related genes.

The methods and materials provided herein can be used to identify genes governing cancer-related phenotypes such as angiogenesis or metastasis. For example, the methods and materials provided herein can be used to identify genes that confer metastatic potential upon non- or low-metastatic potential cancer cells. Briefly, activation/overexpression of certain genes can potently enhance the metastatic potential of various tumor cell types. Some examples of such dominantly acting genes and their relevant cell systems include, without limitation, RhoC overexpression in B16 melanoma cells (Clark et al., Nature, 406(6795):532-5, 2000), VEGF-C overexpression in human breast cancer cells (Skobe et al., Nat. Med., 7(2):192-8, 2001), and TGFβ overexpression in human breast cancer cell lines (Tobin et al., Oncogene, 21(1):108-18, 2002). In these systems, a MaSS screen can be designed to identify mutational events that represent the functional equivalence to these key changes that are required for metastatic potential. For example, a breast cancer cell line can be engineered to exhibit TGFβ-dependent metastatic capability. This can be accomplished by obtaining rtTA and Tet-TGFβ cells whose lung seeding capability is dependent on induction of TGFβ expression via doxycycline administration. Metastatic capability can be assessed by injecting the cells to be tested into a tail vein followed by examining lung tissue for evidence of tumor seeding. After obtaining cells that exhibit TGFβ-dependent metastatic capability, the cells can be genetically manipulated as described herein and then assessed for metastatic capability by, for example, implanting the cells into immuno-deficient animals in the absence of doxycycline and observing the lungs for micro or macro-metastasis. A negative control can be cultures that have not been manipulated where the cultures are injected into animals not treated with doxycycline. A positive control can be the injection of Tet-TGFβcultures into mice treated with doxycycline. Resulting lung metastatic foci can then be harvested, and the TGFβ-equivalent genetic element that has second site suppressed the need for TGFβ overexpression can be identified as described herein.

The methods and materials described herein also can be applied to the analysis of non-cancer pathways, for example, those pathways involved in metabolism, neurodegeneration, lymphocyte activation and maturation (e.g., hematopoietic stem cell development), apoptosis, tissue differentiation, cell adhesion, DNA repair, and cell cycle control. In such screens, the cells can exhibit a dominant phenotype (e.g., cell viability, cell migration, cytokine secretion, expression of certain markers such as CD molecules, or reporter activation) that is governed by a single dominant genetic element. For example, genes that enhance the growth and viability of neural stem cells (NSCs) can be identified.

Briefly, NSCs are dependent on upon EGF for growth and survival in culture. Withdrawal of EGF from the culture media leads to rapid and complete death of the culture. Transduction and expression of an expression construct encoding a constitutively active EGF receptor (EGFR) mutant confers growth and survival in the absence EGF. Thus, NSCs are "one-hit" (e.g., EGF supplementation or induction of EGFR activation) away from a dominant phenotype (e.g., proliferation and survival). The MaSS screen methods and materials described herein can be used to identify EGF/EGFR-equivalent genetic elements. For example, NSC cultures can be engineered to (1) express rtTA and tet-EGF or activated EGFR alleles and (2) show growth in the absence of EGF and presence of doxycycline. These cultures can be genetically manipulated through a variety of standard approaches including, without limitation, proviral insertional mutagenesis, genetic suppression elements, and cDNA complementation. These cultures can be removed from doxycycline. After removal of doxycycline, all cells will cease proliferating and undergo apoptosis except for those cells that have acquired an EGF/EGFR-equivalent genetic element (activated or inactivated by the genetic manipulation) that confers cell growth and survival in an EGF or EGFR independent manner. In other words, cells that survive will harbor one or more genetic events that second-site suppress the loss of EGF/EGFR pathway activation. The identification and pharmacological manipulation of such identified genes can enhance the growth and survival of NSCs and thus improve the potential of cell-based somatic therapies or enhance the expansion and mobilization of NSC pools in vivo that would then improve the repair and recovery of the CNS in the setting of injury or degenerative conditions such as cerebral vasculature accidents, Alzheimer's disease, multiple sclerosis, and others.

Likewise, genes that induce neuronal differentiation and survival can be identified using the methods and materials provided herein. Under well-established conditions, NSCs can be induced to differentiate in vitro into neurons by withdrawing EGF and exposing the cells to brain-derived neurotropic factor (BDNF). These neurons are dependent upon BDNF for their differentiation and survival. Thus, the MaSS screen methods and materials provided herein can be used to identify BDNF-equivalent genes. For example, transgenic animals can be engineered to express inducible alleles of neurotropic factors or their receptors (e.g., Tet-regulated BDNF) in their neurons. NSCs derived from these animals can then be differentiated into neurons by EGF withdrawal and doxycycline exposure since doxycycline will turn on the expression of BDNF. These resulting neuronal cells can then be genetic manipulated via, for example, proviral insertional mutagenesis or cDNA complementation. After the genetic manipulation, the cultures can be removed from doxycycline. After removal of doxycycline, only neurons that harbor integration events that activate BDNF-equivalent genes will be able to survive. Those integration events can then be cloned from the surviving cells by standard molecular techniques.

The methods and materials provided herein can be used to identify genes involved in pancreatic beta cell survival. Primary cultures of purified pancreatic beta cells or the mouse beta TC6-F7 cell line are dependent upon NGF signaling for survival in culture (Perucci et al., *Diabetologia*, 44:1281, 2001). NGF and its receptors, gp140 (Trk-A) and p75 (NTR), are expressed in beta cells where NGF is produced and secreted in a biologically active form. Exposure of these cultures to a neutralizing monoclonal anti-NGF antibody induces apoptosis of beta cells in a transcription/translation independent manner that is mediated by pg140 (Trk-A). Thus, beta cells that are "one-hit" (NGF pathway activation) away from survival can be produced and used in a MaSS screen to identify NGF-equivalent genetic elements that second site suppress the requirement for NGF production. For example, the mouse beta TCF-F7 cell line can be engineered to express rtTA and inducible forms of dominant negative Trk-A or antisense Trk-A (e.g., tet-dn Trk-A or antisense Trk-A) or antisense NGF (tet-antisense NGF) so that a culture of such cells is established that will only grow in the absence of doxycycline (e.g. without activation of the dominant negative form). Next, such cells can then be genetically manipulated via, for example, proviral insertional mutagenesis, genetic suppression elements, or cDNA complementation. Such manipulated cultures can be incubated with doxycycline to turn on the dominant negative forms that will induce apoptosis. All cells will undergo apoptosis except for ones that have one or more genetic elements activated or inactivated by the genetic manipulation that confers cell survival in an NGF-independent manner. In other words, cells that survive this assay will be cells that harbor one or more integration events that activate second-site suppression lesions, for example, NGF-equivalent hits. Some of these may include signaling surrogates of the Trk-A receptor, ligands that engage Trk-A, or core components of anti-apoptotic pathways. Standard techniques can then be applied to identify the genes activated or inactivated by such integration events.

Neutralizing NGF signaling in beta cells also can be accomplished using anti-NGF or anti-Trk-A antibodies in the culture media. Alternatively, neutralization and inducible regulation can be accomplished by knocking out the endogenous NGF gene or Trk-A gene and introducing or knocking-in an inducible allele of the knocked out gene. Standard knock-out and knock-in technologies can be used. In these cases, the addition of doxycycline to the media can permit the continued expression of key components in the NGF loop and therefore permit survival of these cultures. The identified genes can be used to enhance beta islet cells survival during, for example, transplantation procedures.

Figure 3A:
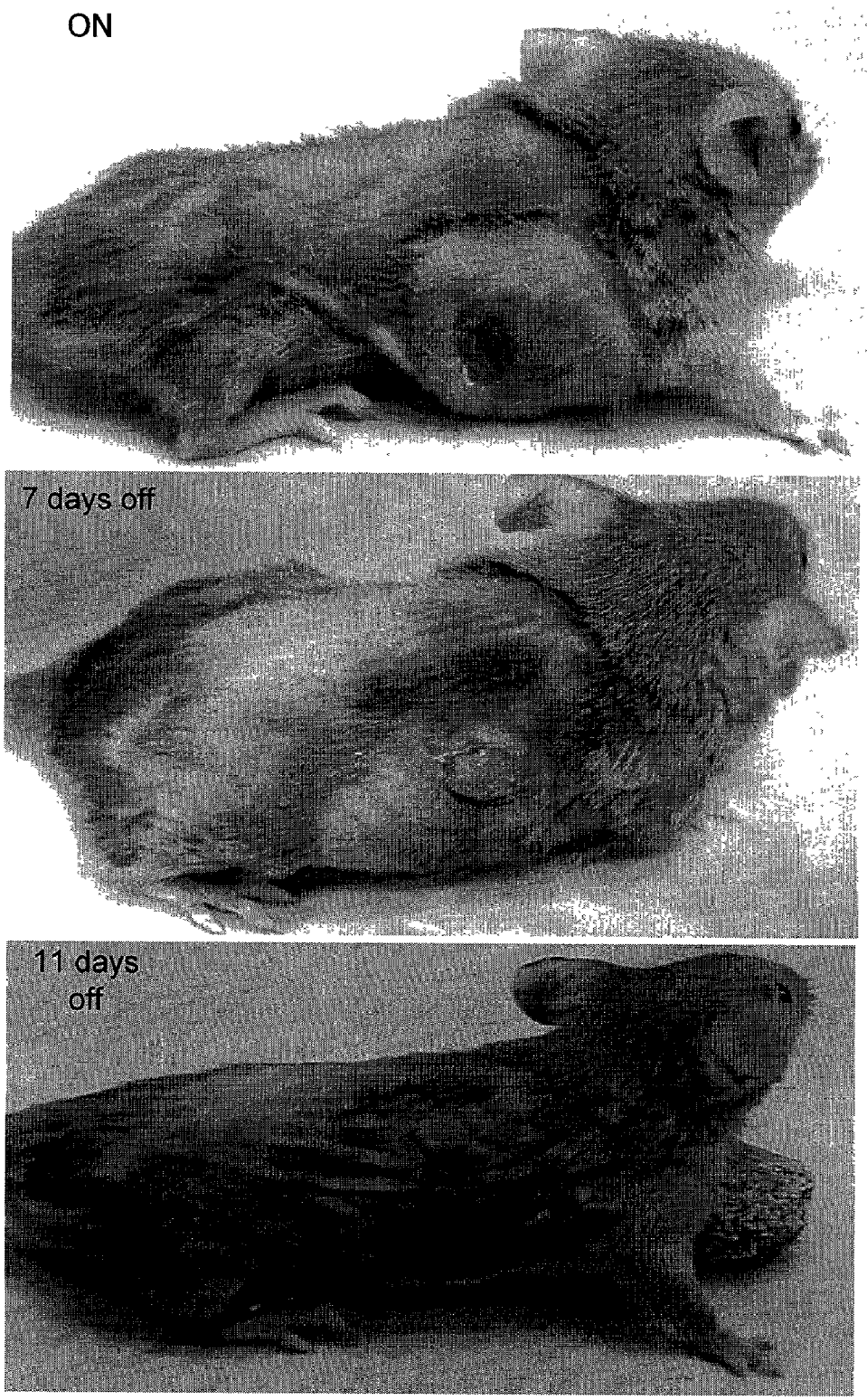
FIG. 3A is a photomicrograph showing the regression of primary cutaneous melanoma in doxycycline-treated Tyr/Tet-Ras Ink4a/Arf−/− mice (null for both $p16^{INK4a}$ and $p19^{ARF}$) after withdrawal of doxycycline in drinking water.
Figure 3B:
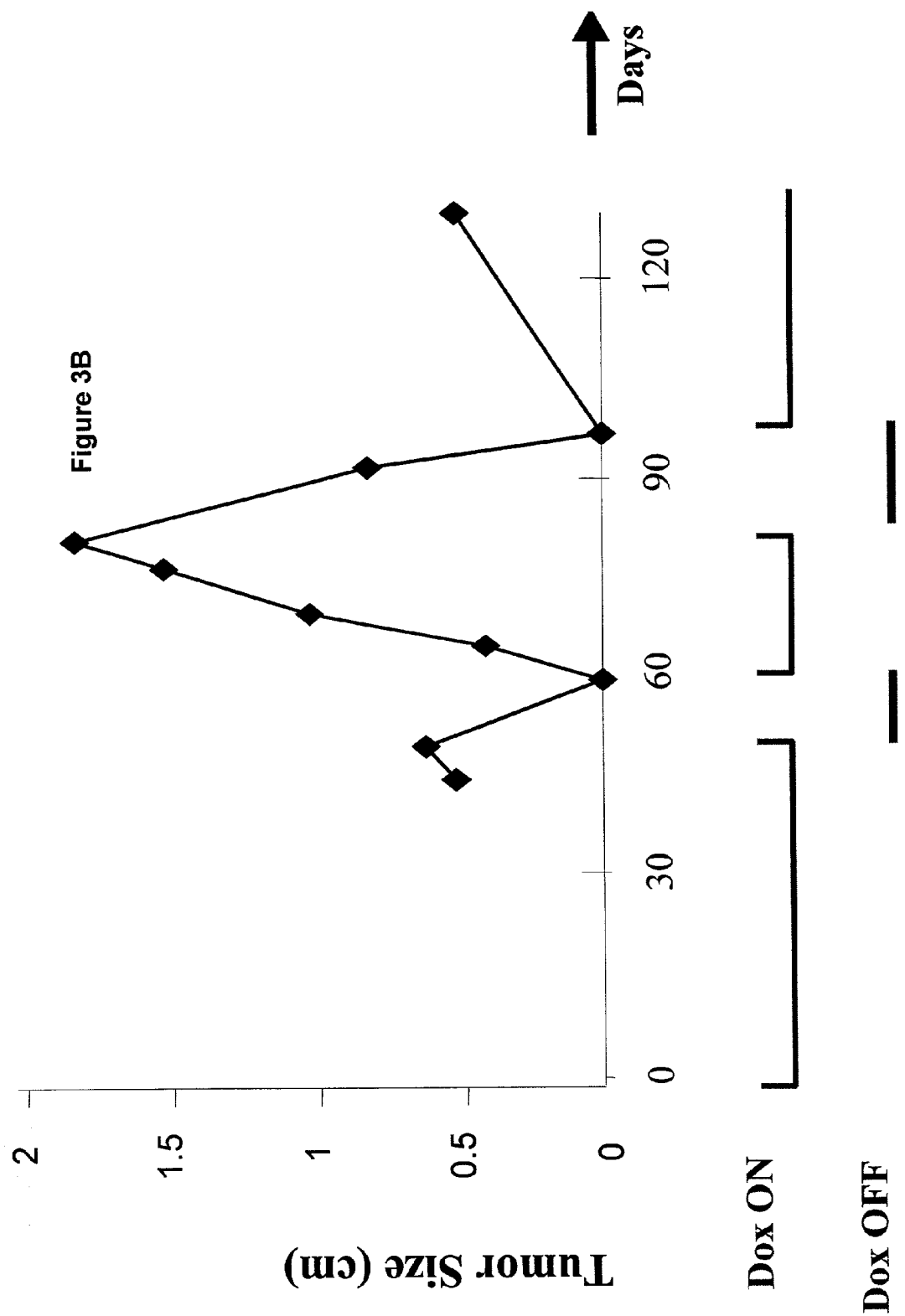
FIG. 3B is a graphical representation of the measurement of tumor size in a Tyr/Tet-RAS Ink4a/Arf−/− mouse (null for both $p16^{INK4a}$ and $p19^{ARF}$) during doxycycline induction and withdrawal.

The methods and materials of the invention have many applications. For example, the methods can be used in screening methods for identifying cancer therapeutics (e.g., antagonists/agonists). In these methods, determination of regression/enhancement of tumor size in an inducible animal model of cancer in the presence of a test compound can be used to identify such antagonists/agonists. Similarly, the effect of a test compound on the level of oncogene mRNA, protein, or activity in the tumor cell lines of the invention can be used to identify the candidate as an agonist or antagonist (see below and FIGS. 3A and 3B). Lastly, the ability to compare the effect of a test compound to that of genetically switching off the inducible oncogene in this system allows the identification of surrogate markers that are predictive of the clinical response to the compound.

The methods of the invention also can be used in the functional validation of candidate genes involved in cancer, for example, genes encoding putative surface receptors or ligands. Specifically, a detailed expression profile of gene expression in tumors undergoing regression or regrowth can be used to identify those factors with plausible links to tumor maintenance. In addition, comparisons of expression profiles in established tumors (during regression/re-emergence in vivo) versus purified cultured tumor cells +/− induction (the latter are free of host cells) can be carried out. Differences in in vivo versus in vitro expression profiles can be used to identify host-derived factors or tumor cell changes brought about by the host microenvironment. For mouse expression profiling, comprehensive screens during tumor regression and cell line induction can be conducted employing a range of techniques. These techniques include the use of suppression subtraction (in cell culture), differential display, proteomic analysis, serial analysis of gene expression (SAGE), and cDNA and/or oligonucleotide microarray analysis on, for example, membranes or glass.

Once desirable candidate factors are identified, expression kinetics can be studied in greater detail using RNA in situ hybridization and immunohistochemistry (MC). These data provide information on which cellular compartment (host or tumor cell) is the source of expression. From a therapeutic standpoint, host-derived factors may prove more useful, given the more static nature of this compartment relative to the ever-changing tumor compartment. Finally, beyond these expression studies, it is possible to exploit this in vivo system to assess the consequences of antibody neutralization, as well as to determine the impact of constitutive expression (mouse or human cDNA) on the cell lines of the invention in tumorigenesis and maintenance in the presence or absence of inducer.

The invention also provides a cell culture system for the identification of tumor-derived angiogenic factors. Adaptation of the tumors cells generated using the methods described herein to culture, as well as their capacity to survive in serum-free conditions, facilitates cell-based functional assays in which secreted factors relevant to cell survival are identified. Further, expression profiling can be used to identify angiogenic factor homologues, based simply on homology with known factors such as proliferin.

The invention is described further below using, as an example, the use of a tetracycline-regulated RAS transgenic mouse possessing activator (Tyrosinase driven reverse tTA, i.e., tet-ON) and reporter (Tet-RAS) transgenes on the INK4a/ARF null background (null for both $P16^{INK4a}$ and $P19^{ARF}$; see FIG. 1) in methods for identifying genes that are involved in the pathogenesis of melanoma. Animals or cells heterozygous for an INK4a/ARF gene mutation that disrupts both $P16^{INK4a}$ and $P19^{ARF}$ are referred to as Ink4a/Arf+/− animals or cells, while animals or cells homozygous for an INK4a/ARF gene mutation that disrupts both $P16^{INK4a}$ and $P19^{ARF}$ are referred to as Ink4a/Arf−/− animals or cells. It is noted that this Tyr/Tet-Ras Ink4a/Arf−/− system is meant only to be exemplary. For example, in addition to melanoma, the methods of the invention can be used to identify genes involved in any stage (e.g., initiation, progression, maintenance, or metastasis) of any other type of cancer. For example, genes that are involved in other skin cancers, as well as lung, prostate, breast, colorectal, liver, pancreatic, brain, testicular, ovarian, uterine, cervical, kidney, thyroid, bladder, esophageal, hematological (e.g., leukemia), and lymphatic cancers, among others, can be identified. Similarly, the example below employs a tetracycline-based system to regulate induction of oncogene expression. Any of a number of other inducible systems (e.g., systems based on a metallothionien promoter or an estrogen receptor), as well as appropriate promoters and cell types, can similarly be used in the invention, and are well known in the art. Also, the example described below employs the ras oncogene, but the invention also includes the use of any other oncogene or (tumor suppressor gene) in these methods, as well as genes that are identified using the methods of the invention.

Building a Mouse Model of Melanoma

Despite the clear association of INK4a/ARF mutations and melanoma predisposition in humans, Ink4a/Arf null mice (null for $p16^{INK4a}$ and $p19^{ARF}$; Ink4a/Arf−/− mice) fail to develop melanomas. It is well known that rodents are resistant to melanoma development. This resistance likely relates in part to species-specific differences in the melanocyte microenvironment. In humans, most melanomas arise within the epidermal microenvironment as in situ lesions in a radial growth phase. Progression towards the vertical growth phase (i.e., downward invasion into the dermis) is thought to require additional genetic alterations that may confer a survival advantage in the less "supportive" dermal mileu. This view derives support from the observation that epidermal melanoma cells do not readily survive and proliferate when transplanted into a dermal microenvironment (Nesbit et al., Oncogene 18:6469, 1999). Since melanocytes of adult mice reside in the dermis, it is conceivable that multiple pro-survival/growth stimulatory signals are required to reach a critical transformation threshold in the mouse. We overcame this high threshold by providing an additional oncogenic stimulus in Ink4a/Arf−/− melanocytes. The oncogenic stimulus that we used first was activated RAS (H-RAS$^{V12G}$).

H-RAS$^{V12G}$ was expressed in melanocytes with the aid of the tyrosinase promoter and an upstream enhancer element (Ganss et al., Embo J. 13:3083, 1994). Against an Ink4a/Arf+/+ background, spontaneous cutaneous melanomas emerged at a very low incidence and with a long latency (Chin et al., supra). Significantly, these rare melanomas showed spontaneous deletion of both Ink4a/Arf alleles. Correspondingly, melanomas arising in Ink4a/Arf heterozygotes sustained a consistent loss of the wild type Ink4a/Arf allele. Finally, on an Ink4a/Arf−/− background, transgenic animals developed spontaneous cutaneous melanomas with high penetrance after a short latency (Chin et al., 1997, supra). Thus, we showed that RAS activation can cooperate with Ink4a/Arf deficiency in vivo to accelerate the genesis of melanoma. Lastly, similar to human melanoma, the p53 gene remained in a wild type configuration in these mouse melanomas (Chin et al., 1997, supra). Thus, the genetic profile of these melanomas recapitulates some of the classical genetic features observed in human melanoma, namely activation of the RAS pathway, deletion of the Ink4a/Arf tumor suppressor, and the absence of a p53 mutation.

Role of Activated RAS in Melanoma Maintenance

Figure 2:
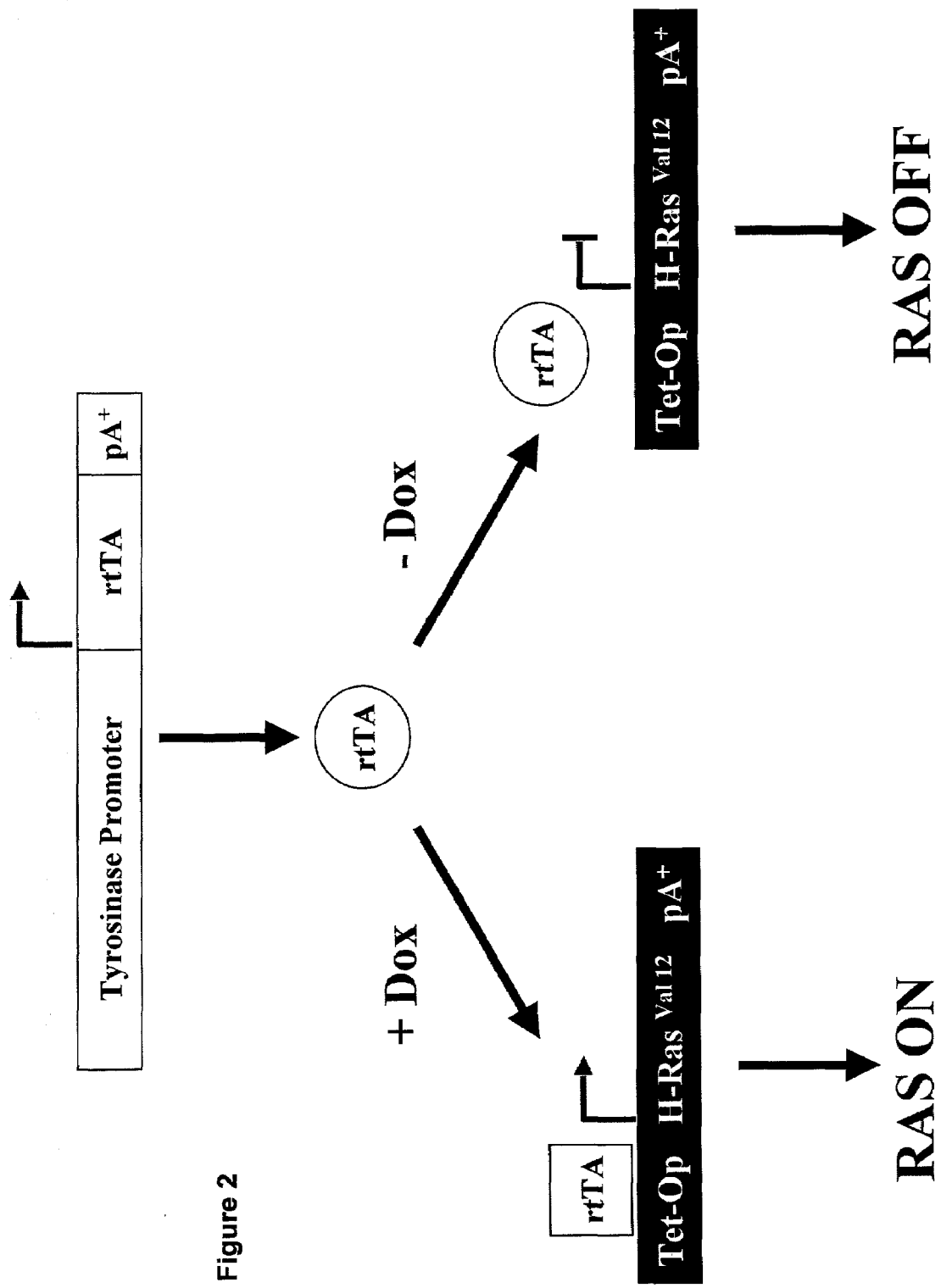
FIG. 2 is a schematic representation of the Tet-regulated system.

To study the role of a dominantly acting oncogene, such as activated RAS, in fully-formed tumors, a conditional H-RAS$^{V12G}$ transgenic model utilizing the tetracycline-regulatory system was established (FIG. 2). The need to assess oncogene function in fully-established tumors arises from the fact that advanced malignancy represents the phenotypic end-point of many successive genetic lesions that impact on the function and regulation of many oncogene and tumor suppressor gene pathways. Hence, it is not clear whether a particular cancer-initiating lesion remains relevant to tumor maintenance and, if so, what that role may be. Particularly important is the concept that one of the "acquired" roles of an inciting oncogenic lesion could be to influence host-tumor interactions that guide such processes as angiogenesis and immune sequestration. To address these issues, the tetracycline (tet) system (Kistner et al., Proc. Natl. Acad. Sci. U.S.A. 93:10933, 1996) was utilized. Specifically, a tet-regulated RAS transgenic mouse (Tyr/Tet-Ras) was generated that possessed both activator (Tyr-rtTA) and reporter (Tet-Ras) transgenes on the Ink4a/Arf−/− background (FIG. 2). Activated RAS expression in this model can be regulated by doxycycline in media or in drinking water in vitro or in vivo, respectively (Chin et al., Nature 400:468, 1999). Moreover, these mice developed spontaneous cutaneous melanomas in a strictly doxycycline-dependent manner, i.e., melanomas arose only in doxycycline-treated Tyr/Tet-RAS Ink4a/Arf−/− mice. These doxycycline-induced tumors shared all of the features of the constitutive Tyr-RAS Ink4a/Arf−/− melanoma model (Chin et al., 1997, supra). Specifically, they presented as amelanotic, invasive, and highly vascular tumors which, upon histological examination, exhibited a spindle morphology with anaplastic and pleiomorphic cytology, strong immunoreactivity to the early melanocyte-specific marker tyrosinase-related protein-1 (TRP-1) (Thomson et al., *J. Invest. Dermatol.* 90(4):459, 1988), and robust H-RAS$^{V12G}$ expression and activity.

When these doxycycline-treated Tyr/Tet-RAS Ink4a/Arf−/− mice, bearing one or multiple independent primary melanomas, were withdrawn from doxycycline administration, established melanomas (0.5 to 1.5 cm in diameter) rapidly regressed to barely detectable or undetectable masses (FIGS. 3A and 3B), with only residual scattered tumor foci being detectable on microscopic examination within 10-14 days. In other words, removal of activated RAS in an established melanoma resulted in tumor regression. Moreover, this regression process was accompanied by activation of apoptosis in both tumor cell and host-derived endothelial cell compartments (Chin et al., 1999, supra). This finding established an essential role for activated RAS not just in tumorigenesis, but in tumor maintenance as well, and suggested a role for activated RAS in sustaining host-tumor cell interactions essential for tumor growth and homeostasis.

RAS-induced Ink4a/Arf−/− Melanoma Cell Lines are Strictly RAS-dependent for Tumorigenicity Independent Tyr/Tet-RAS Ink4a/Arf−/− melanoma cell lines were derived from primary melanomas in doxycycline-supplemented media. These cell lines expressed H-RAS$^{V12G}$ mRNA, protein, and activity in a doxycycline-dependendt manner. Although it did not impact significantly the in vitro growth properties of these cells, continued expression of H-RAS$^{V12G}$ was required for tumorigenicity in vivo, a finding consistent with a role of H-RAS$^{V12G}$ in tumor maintenance. Specifically, subcutaneous or dermal injection of these cells yielded tumors in SCID mice treated with doxycycline with 100% efficiency, while those mice not receiving doxycycline remained tumor-free after many months of observation (Chin et al., 1999, supra). Similarly, anchorage-independent growth, a surrogate for tumorigenicity, is also dependent on RAS activation. Therefore, this model provides a no-background system in which to search for genes capable of complementing the functions of activated RAS in tumorigenesis and tumor maintenance.

In addition, the genomes of Ink4a/Arf deficient tumor cells remain very stable, unlike p53 deficient cells, thus providing a stable cancer gene discovery system. This unique system provides a number of unprecedented opportunities for the identification of cancer targets, particularly those important for tumor maintenance and host-tumor interactions (see below).

Tet-RAS Tumor Cells Support Endothelial Cell Survival In Vitro

Figure 4:
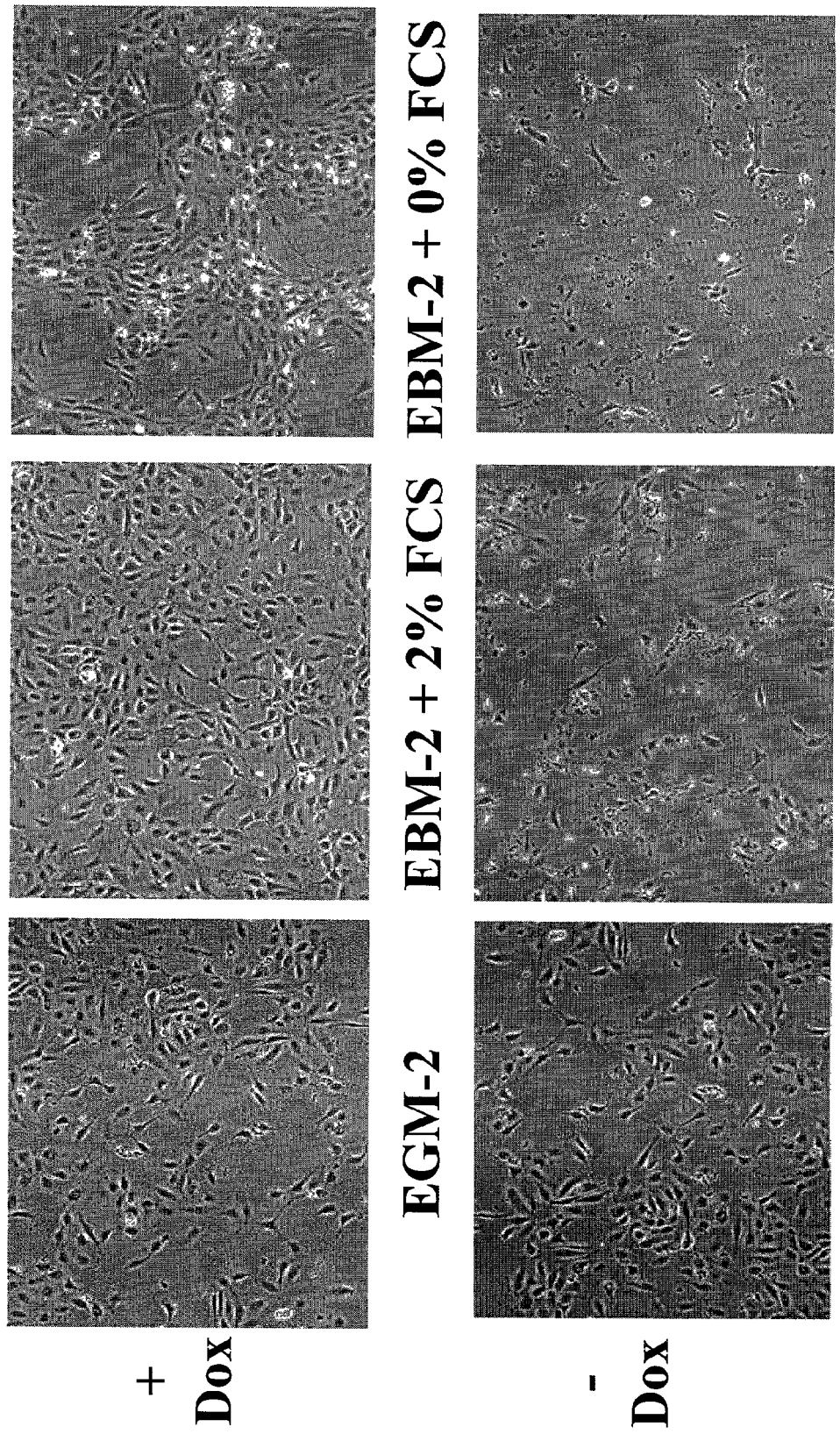
FIG. 4 is a photomicrograph of early passage primary human umbilical vein endothelial cells (HUVEC) in co-culture with Tyr/Tet-Ras Ink4a/Arf−/− melanoma cells (null for both $p16^{INK4a}$ and $p19^{ARF}$) in the presence or absence of doxycycline. EGM-2=fully supplemented media; EBM-2+2% FCS=basal media with 2% FCS; EBM-2+0% FCS=serum-free basal media. Enhanced survivability of HUVEC cells is found in media shared with tumor cells in the presence of doxycycline.

To explore the role of H-RAS$^{V12G}$ in tumor angiogenesis, we have determined that enforced expression of VEGF in SCID explant tumors does not rescue endothelial cell apoptosis, nor reverse tumor regression upon doxycycline withdrawal and consequent down-regulation of H-RAS$^{V12G}$, therefore providing in vivo evidence that the role of H-RAS$^{V12G}$ in tumor maintenance extends beyond regulation of VEGF expression. The findings of loss of host-derived endothelial cell viability upon loss of H-RAS$^{V12G}$ expression in tumor cells suggest that H-RAS$^{V12G}$ expression by the tumor cells leads to a pro-angiogenic state that supports tumor angiogenesis, and that this state collapses once H-RAS$^{V12G}$ expression is turned off by removal of doxycycline. Consistent with this hypothesis, we have shown by in vitro co-culture assay that RAS-expressing melanoma cells indeed secrete paracrine factors capable of enhancing viability of primary human endothelial cells in serum-free conditions (FIG. 4). The studies described herein have characterized the kinetics and phenotypic consequences of RAS down-regulation in vivo and in vitro, and have provided evidence for interaction between tumor cells and host-derived endothelial cells in vivo. As such, this system provides the means to discover oncogene-regulated factors involved in sustaining a tumor-permissive microenvironment, including factors involved in angiogenesis.

The invention provides methods for identifying factors (e.g., polypeptides such as secreted polypeptides) that enhance endothelial cell viability. Such methods can involve culturing endothelial cells (e.g., primary human endothelial cells) under conditions wherein the endothelial cells lack factors necessary for survival. For example, endothelial cells can be cultured in serum-free conditions. After adding a test compound (or a collection of test compounds) produced by RAS-expressing melanoma cells (e.g., melanoma cells from doxycycline-treated Tyr/Tet-Ras Ink4a/Arf−/− mice) to the endothelial cell cultures, the endothelial cells can be monitored for the ability to survive, thereby identifying test compounds that enhance endothelial cell viability. Cell viability can be monitored visually. Test compounds and collections of test compounds can be obtained from RAS-expressing melanoma cell culture supernatant using common protein purification techniques (e.g., affinity chromatography). For example, a culture supernatant can be obtained, and the polypeptides within the supernatant can be fractionated to obtain pools of secreted polypeptides. Positive controls can include co-culturing the endothelial cells with Tyr/Tet-Ras Ink4a/Arf−/− melanoma cells in the presence of doxycycline, while negative controls can include co-culturing the endothelial cells with Tyr/Tet-Ras Ink4a/Arf−/− melanoma cells in the absence of doxycycline.

Identification of RAS Equivalent Loci

Proviral Mutagenesis, a Method of Cancer Gene Discovery

Slow-transforming retroviruses can randomly integrate into the mouse genome and accelerate the development of tumors without being oncogenic themselves. They do so by occasionally activating an endogenous proto-oncogene or, less commonly, disrupting the function of a tumor-suppressor gene, in both cases leading to tumor development. Viral insertions have been used as tags to "fish out" cancer-associated genes, mainly in leukemia and lymphoma models (Bedigian et al., *J. Virol.* 51:586, 1984; van Lohuizen et al., *Cell* 65:737 1991; Haupt et al., *Cell* 65(5):753, 1991; Gilbert et al., *J. Virol.* 67:2083, 1993), but also in breast tumors induced by the mouse mammary tumor virus (Nusse et al., 1982, supra), the latter pointing to the utility of this approach for nonlymphoid cancers. A recent study used such an approach to rapidly identify a vast number of candidate cancer genes in a leukemia-prone model (Li et al., 1999, supra). Using a method based on inverse PCR of proviral genomic sequences, several hundred integration sites were cloned and characterized (Li et al., 1999, supra). To do this, advances in high-throughput sequencing, data analysis, and the rapidly expanding sequence database and refined genetic map of the mouse were exploited. All of the loci previously classified as common integration sites were identified, as well as new common integration sites harboring oncogenes such as H-Ras and genes implicated in the development of tumors in other model systems. Proviral insertion sites included many known genes not previously linked to tumorigenesis, as well as several unknown genes. Most encouraging was the identification of "single" integrations—those represented only once in the collection—into loci encoding transcription factors, kinases, phosphatases, and transmembrane receptors, each with plausible links to established cancer pathways. Given that known oncogenes were identified as targets for single hits, it appears that these screens have not yet reached saturation. In summary, these screens revealed many new integration sites and indicated a multitude of candidate oncogenes that are now in need of validation. Hence, it is now necessary to ascertain whether these genes are truly involved in disease and, if so, to determine their functions and whether they are linked to known cancer pathways. Such properties can be studied in an in vivo cancer model, which has been provided by, for example, the melanoma-prone mouse models of the present invention. Thus, the screening methods provided by the present invention can be used to validate and characterize these and any other candidate oncogenes.

Doxycycline-responsive Melanoma Cells can be Infected by Retrovirus in vitro

Figure 5:
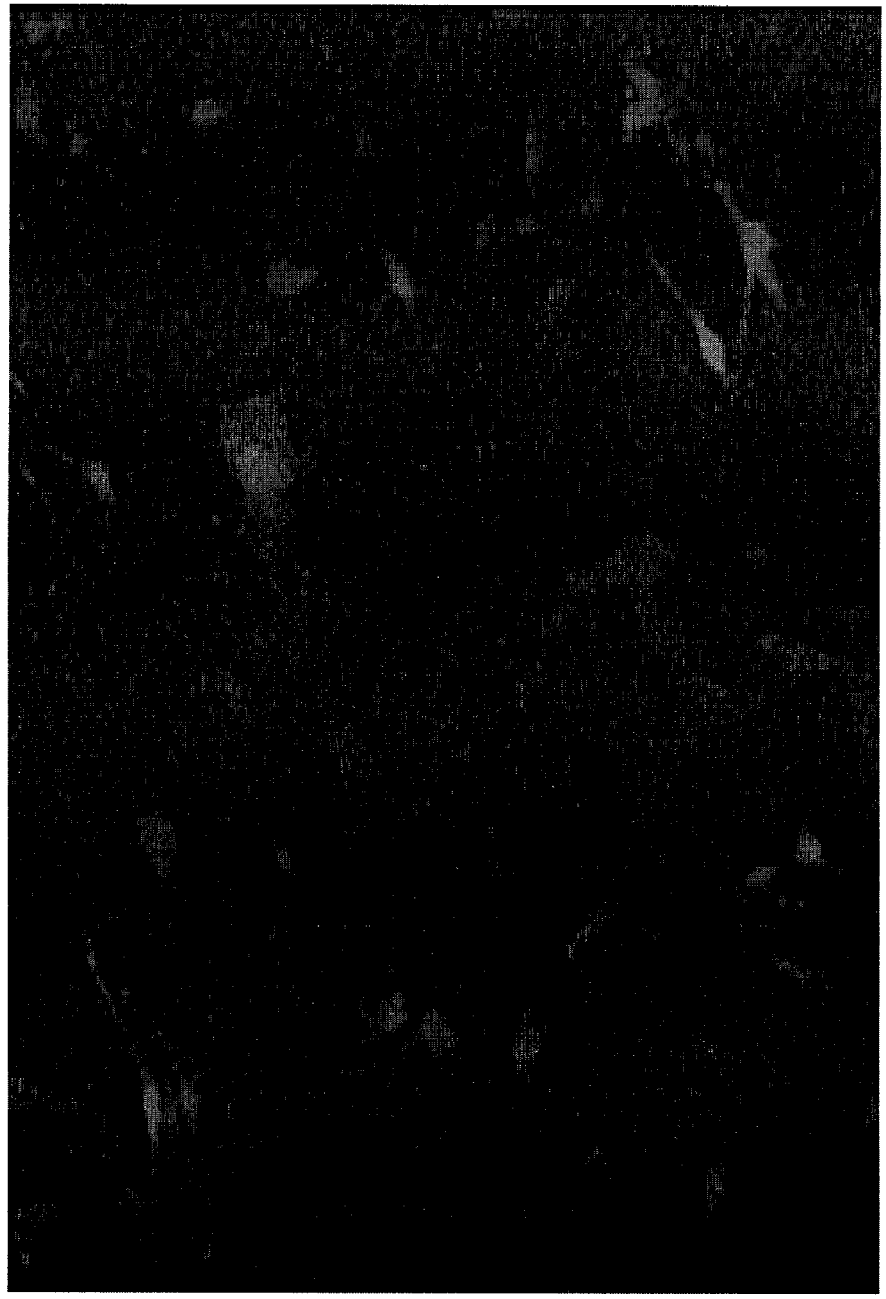
FIG. 5 is a photomicrograph of R545 cells infected with GFP retrovirus.

As is described herein, proviral insertional mutagenesis was used for identifying RAS complementing genes (also referred to herein as "ras equivalent loci" or "REL"). The approach hinges upon efficient proviral infection of the target cell. To this end, Tyr/Tet-RAS Ink4a/Arf−/− melanoma cells were assessed to determine whether they are capable of being infected by retrovirus. A retroviral vector containing a GFP (green fluorescent protein) gene in the pBABE backbone was constructed. GFP-pBABE plasmids were transiently transfected into Pheonix packaging cells. Forty-eight hours after transfection, the viral supernatant was harvested. Exponentially growing doxycycline-responsive melanoma R545 cells were infected with the GFP retrovirus for 12 hours. Thirty-six hours later, infected cells were examined using a fluorescent microscope to determine the efficiency of infection. About 20% of the cells expressed detectable levels of GFP proteins (FIG. 5). Thus, these cells are readily infected by retrovirus. Similarly, R545 cells can be infected by MuLV retrovirus in vitro as determined by Southern blot analysis using a MuLV-specific U3LTR probe. Since integrations of MuLV are random, the expected background smear was observed, presumably representing many different integration events in this non-selected population of cells.

MuLV Infected OFF-Dox Melanoma Cells can Form Tumors in SCID Mice Without Activation of H-RAS Our results showed that SCID mice injected with MuLV-infected OFF-Dox melanoma cells could form tumors in vivo without induction with doxycycline. Specifically, we followed a total of 20 mice injected with 1×10⁶ MuLV-infected OFF-Dox cells at two sites. Within 2 weeks, 18 out of 40 (45%) sites injected with MuLV-infected cells developed measurable tumors (see FIG. 7; Table 1). Many of these tumors presented with a clinical appearance and behavior that was different from that of the RAS-driven parental cells induced on doxycycline. For example, as is shown in FIG. 7, the parental uninfected R545 cell line generated dermal tumors in SCID mice maintained on doxycycline. Tumors typically do not ulcerate until they are beyond 1.5 to 2 cm in diameter. In contrast, in one tumor that emerged 10 days after injection of MuLV-infected OFF-Dox R545 cells, ulceration was apparent even though the tumor only measured 0.4×0.4 cm. The results from this study showed that MuLV-infected OFF-Dox melanoma cells yield tumors in a high percentage of cases (in this experiment it was 45%), facilitating cloning of provirally tagged sequences and subsequent isolation and characterization of provirally activated genes.

TABLE 1

Tumor sizes for tumors that developed within mice at sites injected with MuLV-infected cells.

| No. | Post-injection Tumor size (cm) | | |
|---|---|---|---|
| | 8 Days | 12 Days | 20 Days |
| 1 | 0 × 0 | 0 × 0 | 0.3 × 0.2 |
| 2 | 0.2 × 0.2 | 0.2 × 0.3 | 0.2 × 0.3 |
| 3 | 0 × 0 | >0 × 0 | 0.3 × 0.3 |
| 4 | >0 × 0 | 0.1 × 0.1 | 0.2 × 0.1 |
| 5 | 0.2 × 0.2 | 0.3 × 0.3 | 0.4 × 0.4 |
| 6 | >0 × 0 | 0.4 × 0.5 | 0.4 × 0.5 |
| 7 | 0.5 × 0.4 | 0.5 × 0.4 | 0.6 × 0.5 |
| 8 | 0.1 × 0.1 | 0.2 × 0.1 | 0.3 × 0.3 |
| 9 | >0 × 0 | 0.8 × 0.2 | 0.8 × 0.3 |
| 10 | 0.1 × 0.1 | 0.1 × 0.1 | 0.3 × 0.2 |
| 11 | 0.3 × 0.2 | 0.2 × 0.2 | 0.4 × 0.4 |
| 12 | 0.1 × 0.2 | 0.1 × 0.1 | 0.3 × 0.4 |
| 13 | 0 × 0 | 0.2 × 0.3 | 0.3 × 0.4 |
| 14 | 0.1 × 0.1 | 0.3 × 0.3 | 0.4 × 0.3 |
| 15 | 0 | 0.3 × 0.3 | 0.3 × 0.3 |
| 16 | 0.2 × 0.3 | 0.3 × 0.3 | 0.5 × 0.4 |
| 17 | 0.2 × 0.2 | 0.3 × 0.3 | 0.1 × 0.2 |
| 18 | 0 × 0 | 0.1 × 0.1 | 0.1 × 0.2 |

Figure 8:
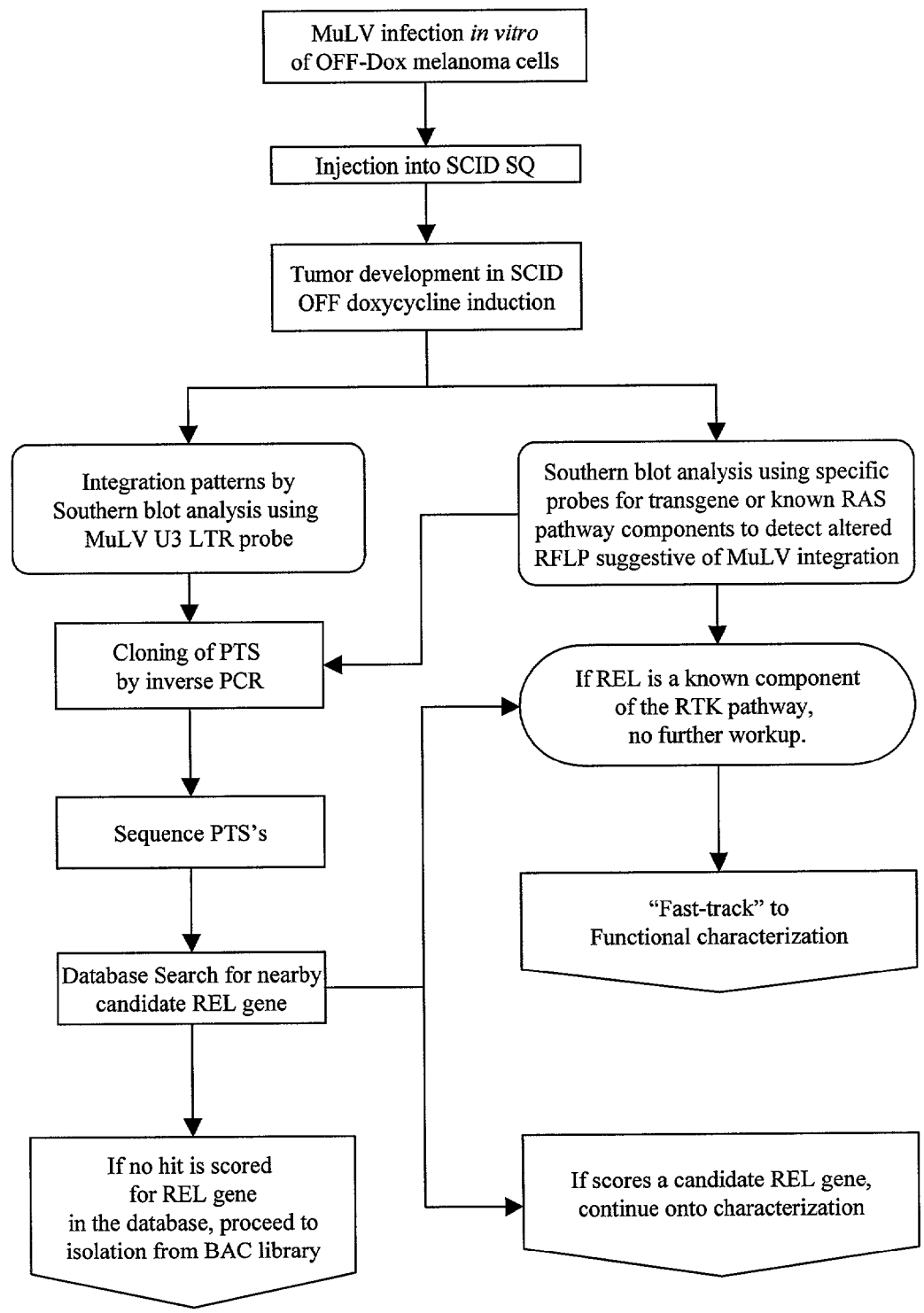
FIG. 8 is a schematic experimental flow-chart for the genetic identification of genes capable of complementing RAS activation in melanoma.

Genetic Identification of Genes Capable of Complementing RAS Activation in Tumor (e.g., Melanoma) Maintenance (see FIG. 8)

Proviral insertional mutagenesis, as described herein, is a method of cancer gene discovery that is particularly well-suited for use in cancer-prone mouse models. Insertional mutagenesis elicits a tumorigenic phenotype either through the activated expression of oncogenes or, less commonly, via the disruption of tumor suppressor genes. Since proviral integration is a relatively random process and "marks" the site of genomic integration, it has emerged as a prime system for the identification of cancer genes. The proviral tagging approach has led to the identification of many new oncogenes and tumor suppressor genes. An abbreviated list includes Pim1, Bmi1, Gfi1, Pal1, and Frat1 in the case of the Eµ-Myc lymphoma system, and Nf1, Mrvi1, Tre2, Meis1, Evi5, and Hoxa9 in the case of the BXH2 myeloid leukemia system. Significantly, this approach, in one experiment, identified all previously catalogued leukemogenic genes in the system, in addition to many unknown genes (Li et al., 1999, supra). Similar strategies have been employed using MMTV for breast cancer genes (Nusse et al., 1982, supra). We have shown that primary mouse melanocytes and astrocytes are susceptible to MuLV infection, demonstrating that this methodology is adaptable to primary non-lymphoid cell types.

The last point illustrates the fact that this invention is applicable to any cancer type, using any inducible gene that is involved in tumor maintenance. For example, glioblastomas arising in a dox-regulated EGFR oncogene mouse can serve as a system for the discovery of EGFR-equivalent genes. If EGFR proves to be important for the maintenance of glioblastoma, then adapting these cells to culture and infecting them with MuLV will yield tumors in SCID mice when the provirus activates a gene equivalent to EGFR.

MuLV Infection

The proviral mutagenesis approach was used in our melanoma system, as follows. Briefly, the OFF-Dox melanoma cell line described above was seeded in culture without doxycycline supplement. During the exponentially growing phase, these OFF-Dox melanoma cells were infected with freshly packaged MuLV viruses. Forty-eight hours after infection, 1-3×10⁶ cells (depending on specific cell lines) were counted from independently infected plates and injected intradermally or subcutaneously into 4-6 week old SCID mice. Each mouse received two injections of cells derived from two independent infections, one on each flank. Control SCID mice were injected with the same number of uninfected OFF-Dox cells that were similarly passaged in culture for the same length of time. All mice were maintained in an uninduced state (i.e., OFF doxycycline, on regular drinking water) and followed closely for the development of dermal tumors. In one study, we observed an about 45% tumor formation rate off doxycycline from MuLV-infected melanoma cells. In order to approach saturation screen, proviral mutagenesis and integration site analysis can be continued until the harvest of new genes/loci diminishes (see below). In another study described below, we observed 100% tumor formation rate off doxycycline from MuLV-infected melanoma cells with 0% tumor formation being observed from uninfected control cells.

Preliminary Assessment of Proviral Integration Sites

FIG. 8 is a flowchart outlining several steps that can be carried out to characterize the proviral integration sites. Taking advantage of the fact that RAS-independent tumors represent clonal expansion of cells harboring MuLV-activated oncogenes, initial characterization of the viral integration sites can begin with Southern blot analysis for an overall integration profile, as well as for an analysis of genes known to be important in RTK-RAS signaling, including RAS (both endogenous and the transgene), Raf, MEK, MAPK/ERK, and P13K. In addition, several growth factors and RTKs implicated in melanoma development can be assessed including, for example, EGFR, bFGF/FGFR, and HGF/SC-MET. EcoRI-, SacII-, or BamHI-digested DNA derived from explant tumors can assayed for polymorphisms in these genes. That such polymorphisms have been generated by proviral integration can be confirmed by comparative genomic analysis of the parental uninfected culture and/or by sequential hybridization with a MuLV-specific U3 LTR probe. If a tumor scores positive for genes previously implicated in melanoma formation, further molecular work-up of this tumor can be suspended and the gene "fast-tracked" for more detailed functional studies (see below). Such hits help point to those growth factors and RTKs with possible physiological relevance to melanoma genesis in vivo. For tumors without proviral integration into known melanoma-relevant loci, a more detailed molecular analysis can be performed, as described below.

Cloning of the Proviral Tagged Sequences (PTS) at the Proviral Integration Sites After Southern blot analyses, molecular analyses can continue with cloning of proviral tagged sequences (PTS) flanking the integration sites. The inverse PCR (IPCR) strategy can be used for this purpose. As is outlined in FIG. 9, analysis of each integration site can entail cloning of two PTS, each flanking the MuLV genome. After DNA from MuLV-induced tumors is digested with restriction enzymes that cut within the provirus (e.g., BamHI and SacII), the PTS are contained on linearized fragments that are tagged with adjacent MuLV-specific sequences. These fragments are re-circularized, and both PTS are PCR-amplified using nested provirus-specific primer sets directed outward from the viral LTR and the restriction site. The resultant amplicons, ranging in size from 500 bp to 14 kb, can be subcloned into a T/A cloning vector. Using standard primers, the PTS can then be sequenced bi-directionally by a high-through sequencing facility. SacII can be used to fragment the genomic DNA, as this enzyme has been shown previously to be over-represented in the CpG islands of gene promoters. Thus, sequencing of SacII-digested PTS more likely yields sequence information residing near relevant gene targets. The number of integration sites amenable to IPCR cloning can be increased by using more than one restriction endonuclease (e.g., BamHI) to cleave the tumor DNA). In this case, to maximally extract information carried within these MuLV-accelerated tumors, the genomic DNA of each MuLV-induced tumor can be fragmented with two (or more) restriction enzymes (e.g., SacII and BamHI), four PTS (two for each of the two restriction digestions) associated with each tumor can be cloned by IPCR (FIG. 9), and bi-directional sequencing of the cloned PTS can then be performed.

Database Search and BAC Filter Screening

Database searches can be performed with genomic sequences of the MuLV-tagged PTS to identify nearby candidate REL genes, as well as to obtain chromosomal localization information. For those with no hits in the database, BAC library screening and cloning can be carried out. It is important to note that proviral integration can occur at some distance from the gene. Therefore, some of these no-database hits may still be near genes that have already been identified in other tumors. Thus, to streamline BAC library screening and sequencing efforts, replica BAC filters containing BACs of frequently targeted loci (e.g., BACs for EGFR, Met, and bFGF) can be generated. In these screens, the IPCR product is assayed for hybridization to the filter. A negative signal warrants cloning and sequencing, while a positive signal obviates further analysis. Hybridization to many clones suggests the presence of repetitive elements and may necessitate the production of a unique probe. BAC clones identified by filter screening as needing detailed sequence analysis can be subject to random shearing, shot-gun subcloning, and high-throughput sequencing, to identify at least one exon.

Figure 10:
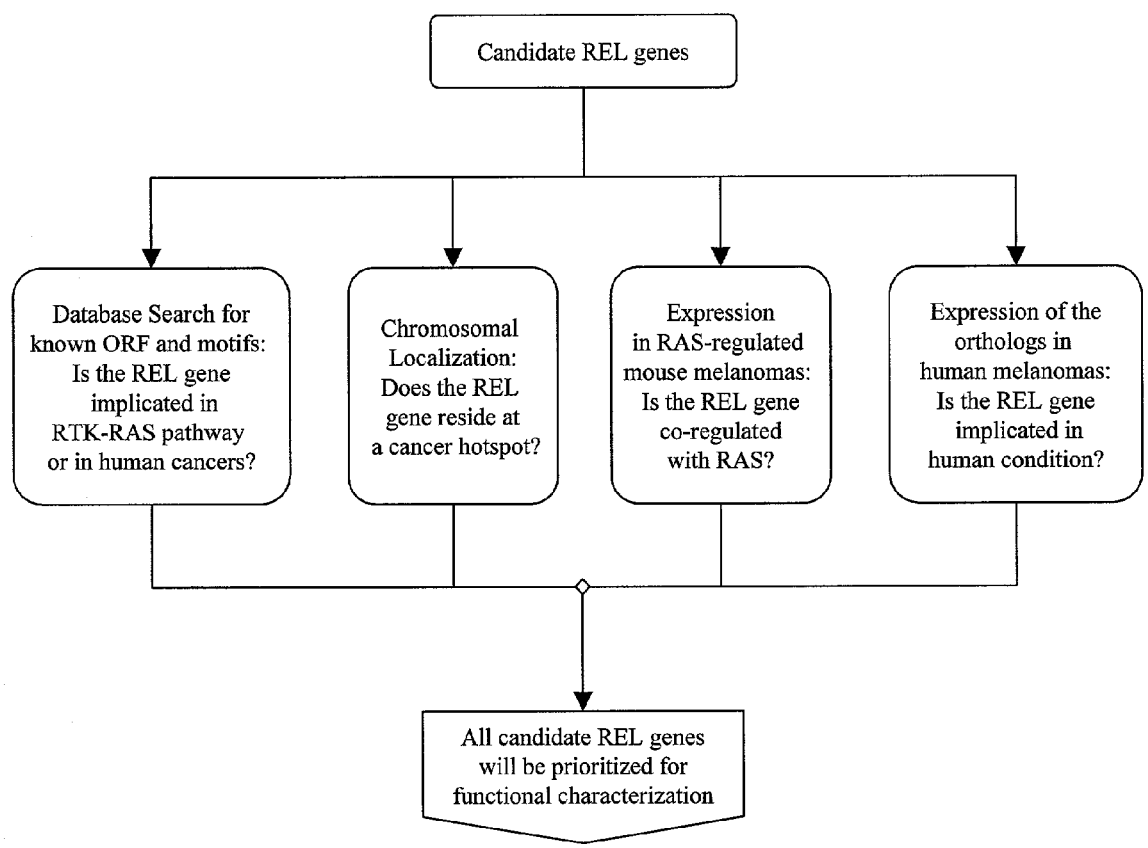
FIG. 10 is a schematic experimental flow-chart for the initial characterization and prioritization of MuLV-targeted ras-equivalent loci (REL).

Initial Characterization and Prioritization of MuLV-targeted REL (see FIG. 10)

Limited characterization of these REL genes can be carried out to prioritize functional characterization efforts. With each sequenced REL gene, the following steps can be taken: (i) database mining to search for informative ORF homology relationships across a large phylogenetic distance, in order identify motifs that enable the classification of putative proteins into functionally relevant groups (e.g., growth factors, transmembrane receptors, RAS superfamily, and adaptor molecules), (ii) chromosomal localization studies to uncover links to known hot spots in human cancers; (iii) expression studies of melanoma gene candidates to determine whether they are modulated by activated RAS transgene expression (i.e., does a regulatory feedback loop exist between the candidate gene and RAS?), and (iv) human melanoma mutational studies to ascertain whether the human ortholog is dysregulated in melanoma and derivative cell lines.

Bioinformatics

With complete or partial candidate REL gene sequences in hand, the entire database can be used to search for homology relationships with genes of known function. Homology searches can be conducted across a large phylogenetic distance to maximize the information yield on potential function and pathway placement of the REL genes. Such efforts can thus lead directly to the identification and/or classification of REL gene products. For example, a portion of these gene products may be components of the RTK-RAS pathway. Although many RTKs have been implicated in the pathogenesis of melanomas, few have been genetically validated. Identification of specific RTKs by this genetic screen allows honing in on those genes and "fast-tracking" them to the functional analyses described herein. Of course, this screen allows similar handling of any putative oncogene, in any cancer type. In cases in which a link to a known gene cannot be established, motif mapping information may still prove to be valuable. For example, the existence of motifs characteristic of RAS super-family members (e.g., the Switch domain I) (reviewed in Malumbres et al., *Frontiers in Biosciences* 3:887, 1998) or RTKs can elevate the importance of a REL for subsequent analyses. Finally, if a putative REL gene product is labeled as a pioneer protein (i.e., it has no homology to anything in the database), determination of how to proceed can be facilitated by analysis of information derived from chromosomal localization and expression studies, which are described below.

Chromosomal Localization

Chromosomal localization of the REL genes can be an important factor in prioritization of clones for detailed functional characterization. Also, in cases in which a neighboring gene is known, if the "locus" proves to be a cytogenetic hotspot in human cancer, then cloning and sequencing of the corresponding BAC could be prioritized. In tumors in which we have an obvious pathogenic hit (e.g., Met), the chromosomal localization of other proviral integrations that are readily derived from database information can be determined. As is mentioned above, many tumors harbor multiple disease-relevant integrations. Specifically, the majority of proviral integrations do not represent background non-pathogenic integrations. To date, it has been found that 20% of these sequences localize to common integration sites or hit genes that are bona fide disease genes.

In most cases, sequence database analyses provide the chromosomal localization of a REL candidate. In all other cases, mapping of the REL candidates can be carried out. Here, the JAX interspecific backcross mapping service can be used. Alternatively, radiation hybrid (RH) panels that are well suited for PCR-based mapping of large numbers of clones can be used. The RH map enables prediction of syntenic regions in humans. However, the need for efforts such as RH mapping will diminish greatly as the database provides complete sequences of the mouse and human genomes.

Expression Pattern Analysis

Using an REL gene as a probe, Northern blot analysis can be carried out not only to reveal the expected size of a transcript, but also to verify that it exhibits an "activated" pattern of expression in a tumor, relative to a parental culture. At a minimum, a prime candidate gene is expressed at much higher levels in the MuLV-induced, RAS-independent melanomas (or other cancer cell types under analysis), or its transcript size may have changed. In addition to verifying tumor-specific activation of the REL gene, its regulatory relationship to RAS can be assessed. Specifically, whether REL gene overexpression correlates with RAS/MAPK activation, as monitored by RAF pull-down assays, or whether doxycycline-induced activation of the RAS transgene alters the expression of that particular REL gene, can be determined. To address the latter issue, the candidate REL gene can be assayed for hybridization to total RNA from SCID mouse explant tumors harvested while ON doxycycline and at various time points after doxycycline was withdrawn (e.g., 6, 12, 24, 36, 48, and 72 hours). Moreover, a prime candidate downstream of RAS will exhibit co-regulation with RAS expression. If a regulatory feedback loop exists, an upstream regulator of RAS, possibly a novel RTK, may also exhibit inverse co-regulation. Finally, one has to bear in mind that proviral integration can lead to inactivation of tumor suppressor genes, thus leading to altered transcript size (truncated non-functional product) or loss of expression.

Expression of Candidate REL Genes in Human Cancer Panels

An important component of the present method involves determination of whether the human ortholog of a REL gene is dysregulated in human cancers, such as melanoma. Again, a similar approach can be used for other cancer maintenance genes, in virtually any cancer type, and such methods are included in the invention.

A first approach to this determination takes advantage of the ability to mine available electronic databases on melanocytes and melanoma for identification of candidate REL genes, for example, searching SAGE data on human melanocytes and melanoma cell lines, generated in a study by the Vogelstein/Kinzler group (Velculescu et al., *Science* 286(5444):1491, 1999). In this study, 3.5 million human transcripts from 19 normal and diseased tissue types were analyzed for their expression levels. For melanocytic lineage, 2 SAGE libraries on normal human melanocytes, and 10 SAGE libraries on human melanoma cell lines were analyzed. These data represent a valuable resource for identification of candidate REL that may be over-expressed in human melanomas. Similarly, expression profiles on melanomas as well as other cancer types have been published in recent years (reviewed in Duggan et al., *Nature Genetics* 1, Suppl:10-14, 1999). In addition to published data, public/NIH-funded databases exist, such as the CGAP database, which contains SAGE libraries for many different types of cancers and normal controls. These databases are available at the U.S. government's National Center for Biotechnology Information web site (e.g., the World Wide Web at ncbi.nlm.nih.gov/ncigap/ or ncbi.nih.gov/SAGE/).

A second approach involves expression screening in human tumor tissues by immunohistochemistry or RNA in situ hybridization on tissue arrays. This can tap into the enormous resources provided by tumor banks such as the Massachusetts General Hospital Tumor Bank (e.g., the Human Melanoma Tumor Bank, which presently contains many samples of melanomas, both invasive and metastatic). Thus, we first order the human ortholog EST and examine its expression by Northern blot analysis. We can also make use of IHC or RNA in situ analysis of tumor sections using tissue array technology. Tissue array technology is a technique in which 100 tumor samples are positioned on conventional pathology glass slides in an array. In this manner, hundreds of tumor samples (of the same type, or of different types) can be screened in one setting, with the same antibody or in situ hybridization probe. Thus, hundreds of specimens, representing a broad spectrum of melanoma subtypes and other cancer types, can be readily screened by tissue array for expression of candidate REL genes. This type of screen can be performed with tissues from any cancer type, obtained from any repositories, private/commercial or public.

Selection of various REL candidates for the functional studies can be based on the profile of the REL gene obtained in the above-described characterization steps. Functional studies are described below.

MaSS Screen Identified Candidate RELs Whose Activation by MuLV Insertion Resulted in RAS-independent Tumorigenicity OFF Doxycycline Doxycycline-responsive RAS-dependent melanoma cells (e.g., R545) derived from Tyr/Tet-RAS Ink4a/Arf-/- animals were maintained in culture without doxycycline supplement and infected with freshly packaged MuLV viruses. Southern blot analysis of infected cells, when probed with MuLV 3' UTR probe, revealed anticipated smears representing random integration of the proviruses into the genome. Forty-eight hours after infection, $1 \times 10^6$ MuLV-infected OFF-Dox cells were injected at two sites into a 4-6 old SCID mouse. Each injection was with cells from an independently infected plate. A total of 20 SCID mice were injected. For control, 20 SCID were injected with uninfected melanoma cells passaged in culture for the same period of time. All animals were observed in un-induced stated (e.g., OFF doxycycline on regular drinking water). Within 4 weeks, 100% of the animals injected with MuLV-infected cells developed measurable tumors (40 tumors in total). In contrast, none of the animals injected with uninfected cells developed tumors, consistent with our previous observation that these derivative melanoma cells remained strictly dependent upon RAS activation for tumorigenicity.

Tumors emerged OFF doxycycline from MuLV-infected cells were harvested and genomic DNA extracted for cloning of the proviral-integration sites by IPCR. DNAs were digested with both BamHI and SacII and subjected IPCR as described herein. IPCR bands were observed after the secondary nested IPCR. Each band represented a clonal proviral-integration site, which is presumed to activate or inactivate a REL to confer these cells doxycycline-independent (RAS-independent) tumorigenicity. These IPCR bands were isolated, purified, and subjected to sequencing.

About 800 IPCR-cloned integration sequences were analyzed, and about 500 yielded informative sequences. From these 500 sequences, BLAST search in both private and public genome databases revealed hits for about 50%. These sequences identified a total of 57 integration sites (Table 2), 19 of which are common (e.g., occurred in at least two tumors). These common integration sites are distributed among different chromosomes, thus ruling out the trivial possibility that provirus has activated the Tet-RAS transgene or the endogenous RAS loci. Indeed, a number of these have direct links to cancer-relevant pathways, such as GTPase activating protein RAS-related; CDEP/Ezrin-like protein; EGF-like domain 6; and latent transforming growth factor beta 4S. Given this is not a saturation screen, it is likely that the remaining 38 single hits represent bonafide REL events. Together, these data provide compelling evidence that MaSS screen functions to identify novel and known genes which can second-site suppress the loss of RAS activation in tumor formation.

TABLE 2

Sequences identified via the MaSS screen.

| Accession Number | Celera gene name | Frequency (n = 40) | Chromosome |
|---|---|---|---|
| LM02B1 | Ankyrin related Fem 1A homologue/(AK005944) putative | 37 | 17 |
| LM18B5 | Transcription factor/Transketolase-PKC-delta | 35 | 14 |
| QLM13A1F | TFIID-Tslp (thymic stromal lymphopoietin/? | 25 | 18 |
| LM25C4 | Histone H2B/Histone 3 | 20 | 13 |
| QLM5A2F | GTPase activating protein Ras related (AF183183)/(AK005574) putative | 18 | 5 |
| LM30D6 | ?/gag polyprotein | 17 | 2 |
| LM15B8 | ?/Methionine Aminopeptidase 2 (or) initiation factor2 associated 67 kDa protein | 15 | 11 |
| LM09A2 | nascentpolypeptide-associated complex alpha polypeptide/(AK010636) putative | 6 | 10 |
| LM15B11 | (XM_049059) hypothetical protein/T17101 probable voltage-activated cation channel | 6 | 14 |
| LM15B7 | Dell Majorsplice variant | 5 | |
| LM32A4 | ORF/unknown | 4 | |
| LM28A6 | gag polyprotein/unknown | 3 | |
| LM29D7 | protein kinase C/unknown | 3 | |
| LM03B2 | CDEP/ezrin-like protein | 2 | |
| LM02A2 | NADH dehydrogenase Fe-S2 | 2 | |
| LM32A2 | Riken cDNA gene | 2 | |
| QLM02A1F | sodium chloride/unknown | 2 | |
| LM22B1 | SRP RNA 3' adenylating enzyme | 2 | |
| QLM4A1R | unknown/Nedd4 WW domain 5 | 2 | |
| LM22D16 | actin binding homologue | 1 | |
| | 11626 protein | 1 | |
| LM34C2 | C612746 gene/unknown | 1 | |
| LM37B8 | CGI-49 protein | 1 | |
| LM05D1 | EGF-like domain 6/unknown | 1 | |
| LM21D7 | elongaction factor 1 gamma | 1 | |
| LM36B7 | GOP diss inhibitor 3/unknown | 1 | |
| LM32D6 | GRLP1-glut repeat protein 1 | 1 | |
| LM29D17 | high mobility group protein | 1 | |
| LM27A1 | high mobility/hOAT4 | 1 | |
| LM02B6 | hypothetical protein FLJ11857 | 1 | |
| LM28D9 | hypothetical protein FLJ13287 | 1 | |
| LM31A2 | hypothetical/ORF-integrase | 1 | |
| LM27D4 | KIAA1326 protein/hypothetical latent transforming growth factor beta 4S | 1 | |
| LM37B10 | KIAA1244 (sec related) | 1 | |
| LM32D8 | myosin heavy chain polypeptide 9 | 1 | |
| LM11D2 | NAC-1 | 1 | |
| LM30D11 | neurexin II | 1 | |
| LM25D6 | nuclear factor kappa/Riken cDNA | 1 | |

TABLE 2-continued

Sequences identified via the MaSS screen.

| Accession Number | Celera gene name | Frequency (n = 40) | Chromosome |
|---|---|---|---|
|  | olfactory receptor/ORF-integrase | 1 |  |
| LM37D7 | olfactory receptor 17/olfactor receptor | 1 |  |
|  | P91a/40S ribosomal protein | 1 |  |
|  | Ppic/PR zinc finger protein 6 | 1 |  |
| LM31A3 | putative | 1 |  |
| LM30B6 | putative/hypothetical FLJ13297 | 1 |  |
| LM06B3 | putative/rho associated kinase | 1 |  |
| LM13B5 | putative/RNA binding protein 10 | 1 |  |
| LM32A6 | putative/putative | 1 |  |
| LM11A5 | REV1/lymphoid nuclear protein | 1 |  |
|  | Rpll3a 60S ribosomal protein | 1 |  |
| LM02B2 | scavenger receptor/protease | 1 |  |
| LM33D5 | synaptojanin 2 | 1 |  |
|  | unknown/hypothetical | 1 |  |
| LM25D9 | unknown/aldh3a2 alcohol dehydrogenase | 1 |  |
| LM29B9 | unknown/G3P dehydrogenase | 1 |  |
| LM28D8 | unknown/Ku70 | 1 |  |
|  | unnamed protein/immunoglobulin | 1 |  |

Figure 11:
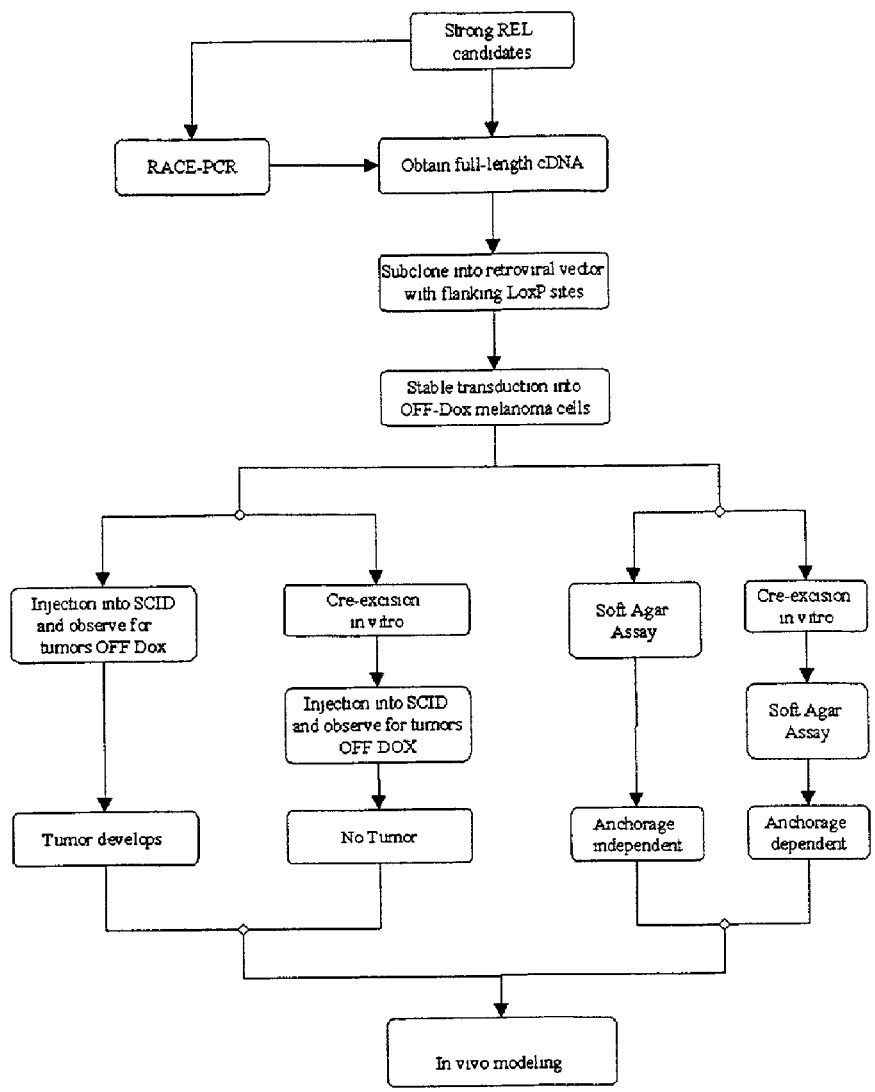
FIG. 11 is a schematic experimental flow-chart for the functional characterization of REL with the goal of identifying prime candidates for detailed in vivo analysis.

Functional Characterization of REL Genes for Identifying Prime Candidates for Detailed In Vivo Analysis (see FIG. 11)

With the identification of candidate REL genes comes the need to verify their pathogenic roles in melanoma genesis, and to elucidate ultimately their mechanism of action. With so many REL gene candidates necessitating characterization, those genes with the most plausible link to cancer pathogenesis, and in particular cancer maintenance, may be pursued using, as an initial approach, cell culture-based studies.

cDNA Production

To perform in vitro functional analysis, cDNA clones having the full-length ORFs can be used. Such full-length cDNAs can be generated using PCR-based method. To accomplish this, the 5' and 3' RACE PCR methodology (Clonetech system) can be utilized, which is a well-established technique that has been used extensively. The source of the mRNA can be the specific SCID explant tumor bearing proviral activation and up-regulation of the particular gene to be cloned. Knowledge of the genomic sequence of the REL gene from either the database or our BAC sequencing efforts can facilitate primer selection.

Stable Retroviral Transduction into Parental OFF-doxycycline Melanoma Cell Lines and Primary Melanocyte Cultures Once a full-length ORF is isolated for an REL candidate, it can be subcloned into a retroviral backbone containing the gene cassette that is flanked by LoxP sites. Retrovirus is produced using the 293T packaging cell line, and the retroviral supernatant is used to infect parental OFF-Dox melanoma cells or other primary non-transformed cells (such as melanocytes or astrocytes) for functional studies. The establishment of stably transduced cell lines is achieved by puromycin selection. Following selection, it is demonstrated that the transduced REL gene is expressed at high levels. Alternatively, ORFs can be cloned into other expression constructs and introduced into such cells by transfection.

Characterization of REL-expressing Melanoma Cell Lines

REL-transduced OFF-Dox melanoma cell lines can be subjected to characterization on multiple levels, including proliferation, survival, migration, immortalization, and anchorage-independence. These studies can be performed with the parental (untransduced) OFF-Dox cell lines, as well as with REL-transduced cultures, with and without Cre-excision. Cre-induced deletion of the REL ORF serves as an important control to ascertain whether the observed phenotype is due to over-expression of a REL gene, rather than integration of the REL-expressing retrovirus. This can be accomplished by transient transfection of a Cre-GFP fusion construct, followed by FACS. Our experience with this approach in cell culture has shown that 100% of GFP+ cells experience loxP recombination/deletion. Thus, by sorting for GFP− and GFP+ cells, we can determine the precise contribution of REL gene expression to the phenotypes uncovered in the above-described analyses, all within the same population of cells. The assays used to characterize these cells are described below.

Proliferation and Survival

Growth of REL-expressing melanoma cells and controls is examined in media containing 10%, 2.5%, and 0.5% serum. Growth curves over 10 to 14 day periods can be analyzed by cell counts on days 0, 1, 3, 5, 7, 9, 11, and 13. Quantitative measure of S phase progression can be determined by BrdU incorporation. These two assays provide both static and dynamic views of the proliferative history of these cells. For example, if the REL-expressing culture has a higher S phase percentage than the Cre-excised control, as measured by BrdU incorporation, and yet their growth curves are overlapping, this suggests that, although REL-expression leads to increased S phase progression, there must be increased death, resulting in similar growth curves. To determine the rate of apoptosis in low and high serum conditions, Annexin V staining by FACS can be performed. Alternatively, cells can be seeded in chamber slides and fixed in methanol: acetone for TUNEL staining.

Migration

To determine whether REL expression enhances invasive capability, Boyden chamber assays can be performed to measure the migration of REL-expressing cells and controls (Shimizu et al., *Biochem. Biophys. Res. Comm.* 264:751, 1999). Briefly, the lower well of a chamber is filled with 600 μl of medium with 10% or 2.5% FCS, and the upper well is seeded with 400 μl of cell suspension. A cellulose acetate membrane filter is then interposed between the two chambers. The chambers are kept in a humidified atmosphere of 5% $CO_2$ at 37° C. for 4 hours. Filters are then washed, fixed with methanol: acetone, and stained with crystal violet. The number of cells that migrate into the filter and reach its lower side can be determined microscopically. Triplicate assays can be performed for each cell line and its controls.

Immortalization

It is likely that REL-expressing OFF-Dox melanoma cells have increased ease of immortalization. Thus, a low-density seeding assay can be used as a surrogate assay for immortalization potential. In this assay, 2500 cells are seeded per well in a 6 well plate. Cells with high potential for immortalization are able to grow to form visible colonies in 14 days. The number of emerging colonies can be used as a quantitative measure for the immortalization potential of those cells.

Anchorage Independence

Since a given REL is likely to be an oncogene capable of promoting melanoma genesis with and without other cooperating mutations, REL-expressing melanoma cells are likely to exhibit anchorage-independent growth. Since anchorage independence is a strong predictor for tumorigenicity in SCID explants, soft-agar assays can be performed. In soft-agar, 10,000 cells are seeded per well in a 6-well plate. Colony formation is monitored daily by microscopic inspection. Cell clusters of greater than 0.5 mm in size are counted as a colony. The number of colonies is a quantitative marker for the tumorigenic potential of the cells.

In Vivo Tumor Formation in SCID Explant Model

Those REL candidates that can confer melanoma cell lines with anchorage-independent growth can be further evaluated for tumorigenicity in a SCID explant model. Specifically, $1\times10^6$ REL-transduced melanoma cells are injected in each of two flanks of SCID mice, and melanoma development is observed OFF doxycycline. To ensure that the tumorigenic phenotype is indeed a consequence of REL overexpression, rather than retroviral integration, a Cre-excised counterpart is injected similarly into SCID mice, and melanoma development is observed at the same time.

While uninduced tumor cells that have sustained numerous primary and secondary genomic changes (i.e., one step away from tumorigenic potential) can be used for these experiments, in vitro functional studies can also be performed using REL-expressing primary non-transformed cells (in this case melanocytes) to obtain information as to the functions of the REL candidates, and aid in the selection of candidates for the in vivo genetic validation. This can be accomplished using standard transgenesis and gene targeting technology.

Characterization of REL-expressing Primary Melanocytes

Growth kinetics, growth factor dependence, survival potential, migration behavior, and immortalization can be assessed in primary melanocyte cultures. These assays can be performed as is described above for REL-transduced OFF-Dox melanoma cells. Similar to studies in parental Off-doxycycline melanoma cells, an important control is examination of transduced cultures with and without Cre-induced deletion of the REL ORF. However, it is difficult to perform such studies in primary melanocyte cultures, given their low transfection efficiency. In other words, delivery of Cre recombinase may be too inefficient to achieve Cre-induced deletion of the REL ORF to perform the control experiment.

As an alternative, the avian retroviral receptor (tVA) system developed by Harold Varmus (reviewed in Fisher et al., *Oncogene* 18(38):5253, 1999) can be employed. Specifically, transgenic mice bearing a tyrosinase-tVA cassette can be generated. These transgenic mice express the avian retroviral receptors in their melanocytes. Thus, primary cultures of these melanocytes can be infected with RCAS virus expressing Cre-recombinase. These primary melanocytes are first infected with retrovirus expressing an REL ORF, and then are selected for stable transduction. Transduced lines are subjected to the experiments described above, after infection with RCAS virus expressing Cre-GFP or GFP alone.

Mechanism of Action of a Candidate REL by Establishing Genome-wide Expression Profiles In addition to the functional studies in cell culture and SCID explants, the mechanism of action of a candidate REL can be uncovered by establishing genome-wide expression profiles of REL-transduced melanocyte cultures with or without Cre-excision. By looking for patterns of gene activation, one can elucidate the mechanism of action. For example, activation of cell cycle genes may suggest a role as a cell cycle regulator, or turning on of known apoptotic mediators in the p53 dependent or FAS-dependent pathways may point to a role in apoptosis. In addition, the information base generated from this kind of experiment may prove to be useful in generating a signature profile for that REL gene, and facilitate the triage of primary tumors as described above.

In Vivo Validation of Candidate REL Genes via Transgenesis

Compelling REL gene candidates based on initial and functional characterization, as described herein, can be assayed for their melanoma-genic potential in vivo. Of course, the various steps from cloning and sequencing of the PTS to characterization of the candidate genes described above are applicable for other tumor maintenance genes, in other cancer types, i.e., genes discovered in the melanoma system can be assayed for their ability to generate or maintain cancer in other cell types. Similarly, genes discovered in other cancer systems can be tested in the melanoma system or other cancer systems. For example, REL genes can be selected for in vivo validation, and in vivo transgenesis and characterization efforts can be initiated subsequently. Briefly, melanocyte-specific expression of the REL gene can be achieved by use of the tyrosinase promoter and enhancer elements, designated Tyr-REL. The capacity of Tyr-REL transgenes to have impact on melanocyte growth and survival and to affect the malignant transformation of melanocytes can be examined in vivo using wild-type or tumor suppressor null backgrounds (e.g., Ink4a/Arf+/+ or Ink4a/Arf−/− backgrounds).

Generation and Establishment of the Transgenic Colonies

Utilizing the tyrosinase enhancer-promoter elements, REL expression can be directed to melanocytes. This promoter has been successfully used to generate Tyr-RAS, Tyr-cyclin D1, Tyr-CDK4, and Tyr-rtTA transgenic animals. It has been shown to confer copy-number dependent expression of the reporter gene. The REL ORF is first subcloned into a CPV1 vector 5' to the SV40 PA. Subsequently, the REL ORF/PA+ cassette is isolated and ligated to the tyrosinase enhancer/promoter element. To accelerate and streamline the establishment of these colonies, the Tyr-REL constructs are injected directly into fertilized eggs harvested from wild-type FVB females impregnated by vasectomized Ink4a/Arf−/− males on an FVB background. Genotyping services that utilize PCR-based screens can be employed. Importantly, initial founders and F1 offspring can be confirmed by Southern blot analysis, rather than by PCR. Once founder lines are established, they can be crossed to Ink4a/

Arf+/− mating partners to generate REL transgenic mice on an Ink4a/Arf+/+ and Ink4a/Arf−/− background. This mating scheme eliminates one generation of mating before producing animals of the desired genotype, thereby reducing time, effort, and cage costs.

Verification of Transgene Expression In Vivo

In addition to documentation of transgene integration and determination of copy numbers by Southern blot analysis, it can be confirmed that the REL transcript is produced in the targeted cell type (e.g., melanocytes) by RNA in situ hybridization. Ribovectors can be constructed that contain average insert sizes of ~300 bp and are judged to be free of repetitive elements by Northern blot analysis. In vitro transcription using a 3′ promoter can be used to generate the necessary anti-sense RNA probe for hybridization to the tissue section, and controls can be the sense transcript. Both digoxen-labeled and radio-labeled riboprobes can be used. The advantage of using the digoxen-labeled in situ hybridization is speed, while sensitivity of radiolabeled riboprobes is much better. Specifically, the transgenic and non-transgenic littermates can be biopsied for skin samples. Tissues are fixed in 4% paraformaldehyde for 24 hours, equilibrated in 17% sucrose solution for 48 hours, encased in OCT™ and then snapped-frozen in LN2 to generate OCT tissue blocks. These skin OCT blocks are sectioned to 5 μm thickness and used for RNA in situ hybridization. Consecutive sections are stained for H&E to evaluate morphology, and anti-TRP1 IHC for melanocytes.

As an alternative to a constitutive Tyr-REL transgenic, a REL transgenic mouse with the REL gene under the control of an inducible system, such as the tet-operon promoter (TetO) can be generated. Once TetO-REL mice are established, the founders can be crossed onto an existing Tyr-rtTA transgenic line. Mice harboring both Tyr-rtTA and TetO-REL transgenes can be induced to express the REL gene by administration of doxycycline in their drinking water. This conditional expression system has been successfully utilized to generate the inducible RAS-expressing melanoma model from which the parental OFF-doxycycline melanoma cell lines were derived, as is described above. Specifically, double transgenic mice (Tyr/TetO-REL) can be induced to express an REL gene postnatally in dermal melanocytes. Expression of REL transcripts in target cells can be confirmed by in situ hybridization of skin biopsies before and after induction with doxycycline drinking water as described above. Once confirmed, subsequent experiments described below for constitutive Tyr-REL transgenics can be performed similarly in the inducible Tyr/TetO-REL transgenic animals.

Functional Characterization of REL in Pre-malignant Melanocytes In Vitro

To determine the function of an REL gene in non-transformed cells, the biological consequences of its overexpression in pre-malignant melanocytes can be examined in primary murine melanocyte cultures. Specifically, newborn mice are sacrificed and skin harvested. After sterilization, the epidermis is separated from the dermis to avoid contamination by dermal fibroblasts. The epidermal layer is then mechanically disrupted, minced, and plated onto a feeder cell layer consisting of mitomycin-treated, growth-arrested XB2 keratinocytes. After about 2 weeks, with sub-culturing, pure melanocyte cultures can be established. With this technique, primary cultures can be generated from litters produced by, for example, (REL+, Ink4a/Arf+/−)× (REL−, Ink4a/Arf+/−) crosses to obtain melanocytes of all genotypes. Once these primary cultures are established, they can be subjected to assays designed to characterize their growth, survival, migration, and immortalization properties, as described herein. In addition, since activated RAS in cells possessing intact mortality pathways has been shown to induce premature senescence, senescence can be monitored by morphology (flattened appearance, hypermelanization in pigmented melanocytes, and growth arrest) in REL expressing cells of Ink4a/Arf+/+ and Ink4a/Arf−/− backgrounds.

Characterization of REL-induced Melanomas in vivo

Melanoma development in Tyr-REL transgenic mice is followed carefully over time. Serial skin biopsies in locations such as ears and tails (preferred locations of occurrence in Tyr-RAS transgenic mice in FVB background) can be performed in small cohorts of animals (e.g., 10 in each genotype group) every month in order to detect pre-malignant lesions and early melanomas. Once clinically apparent tumors emerge, excisional or incisioinal biopsies can be performed to obtain samples for pathological characterization, as well as establishment of cell lines (see below). These can include anti-TRP1 staining for melanocytes, Ki67 for proliferative index, TUNEL for apoptosis, and PECAM staining for vasculature. Furthermore, REL expression can be documented by Northern blot analysis. In addition, for REL genes that are thought to be upstream of RAS, tumor lysates can be analyzed for activated RAS activity, by IP-Western for RAF-binding RAS. Moreover, loci known to be involved in tumor promotion and suppression can be examined, including p53 and PTEN.

Genomic Characterization of REL-induced Melanomas

As an additional level of validation, the global genomic alterations incurred in RAS-induced melanomas can be examined by comparative genomic hybridization (CGH) in order to identify syntenic regions of changes that have been implicated in human melanomas. Our preliminary analysis of 27 mouse melanomas arisen in both the constitutive and inducible melanoma models on both Ink4a/Arf−/− and p53 mutant backgrounds revealed frequent gains of chromosomes 8, 11, and 15, all containing regions syntenic to those known to be amplified in human melanomas. For example, chromosome 11 contains EGFR, a RTK known to be overexpressed in human melanomas. On gene, another candidate implicated in acral lentigenous melanomas in human. Furthermore, the genomic alterations in REL-induced melanomas can be examined by CGH. These studies characterize chromosomal gain and loss in REL-induced in regions syntenic to those altered in human melanomas. Moreover, the profile of genomic alterations in REL-induced tumors can be compared to that of RAS-induced melanomas, to identify common alterations accompanying activation of the RAS pathway.

Molecular Characterization of REL Gene in Non-transformed and Transformed Melanocytes In Vitro Primary tumors can be adapted to culture to establish cell lines for biochemical studies, in order to further characterize the mechanism of action of the REL gene product. For example, the REL subcellular localization can be assessed to understand how it influences the activity of the RAS-MAPK and P13-K pathways. Such studies can begin with the generation of rabbit anti-REL antisera. Once available, immunofluorescent staining for REL in both pre-malignant and malignant melanocytes expressing REL can be examined with respect to cell cycle on, for example, Ink4a/Arf+/+ and Ink4a/Arf−/− backgrounds. Activation of the RAS-MEK-MAPK/ERK pathway can be evaluated by employing the kinase assay for MAPK activity.

Ultimately, the results that are obtained from these transgenic models can be integrated with the bioinformatic data derived as described herein. This can help to delineate the RAS signaling pathway in the process of tumorigenesis, specifically melanoma genesis. The results can also help in assessing the functional and genetic relationship between components of this pathway, and whether global expression patterns can pinpoint its activation or inactivation. The same approach can be applied to other signaling pathways in systems in which other inducible cancer-relevant signaling molecules are used.

The present invention has been described by reference to specific examples of modes for the practice of the invention. It will be appreciated by those of skill in the art that, in light of the present disclosure, numerous modifications and changes can be made to the particular embodiments exemplified without departing from the intended scope of the invention. All such modifications are intended to be included within the scope of the appended claims.

All publications, patents, and patent applications mentioned herein are hereby incorporated by reference in their entirety to the same extent as if each individual publication, patent, or patent application was specifically and individually indicated to be incorporated by reference.

Other embodiments are within the following claims.

What is claimed is:

1. A method of identifying a gene whose activation or inactivation bypasses a cell's dependency on an exogenous oncogene for tumorigenicity, said method comprising:
   (a) providing tumor cells ex vivo, said tumor cells being mouse tumor cells, said cells comprising said exogenous oncogene operatively linked to a promoter regulated by a reverse tetracycline transactivator, said oncogene conferring tumorigenicity when expression is switched on;
   (b) causing said oncogene to be switched off thereby causing said cells to be one mutation away from tumorigenicity;
   (c) introducing a retroviral vector into said cells;
   (d) introducing said cells into an injection site on an immunocompromised mouse, and monitoring the mouse for formation of a tumor at the injection site; and
   (e) identifying, as said gene whose activation or inactivation bypasses a cell's dependency on said exogenous oncogene for tumorigenicity, a gene displaying increased or decreased expression in said tumor as a result of introduction of the retroviral vector.

2. The method of claim 1, wherein said oncogene is an activated ras gene.

3. The method of claim 1, wherein the cells in step (a) are homozygous null for an endogenous tumor suppressor gene.

4. The method of claim 3, wherein said tumor suppressor gene is an INK4a/Arf gene.

5. The method of claim 1, wherein the cells in step (a) are transformed melanocytes.

6. The method of claim 1, wherein the cells in step (a) comprise:
   (a) a first expression construct comprising a gene encoding a reverse tetracycline transactivator operably linked to a tissue-specific or a cell type-specific promoter; and
   (b) a second expression construct comprising said oncogene operably linked to a promoter regulated by said reverse tetracycline transactivator.

7. The method of claim 6, wherein said tissue-specific or cell type-specific promoter is a tyrosinase promoter.

* * * * *